United States Patent
Boriack et al.

(10) Patent No.: US 6,646,102 B2
(45) Date of Patent: Nov. 11, 2003

(54) PROCESS FOR MANUFACTURING AN ALPHA-DIHYDROXY DERIVATIVE AND EPOXY RESINS PREPARED THEREFROM

(75) Inventors: Clinton J. Boriack, Jones Creek, TX (US); Zeng K. Liao, Lake Jackson, TX (US); Thomas H. Kalantar, Midland, MI (US)

(73) Assignee: Dow Global Technologies Inc., Midland, MI (US)

(*) Notice: Subject to any disclaimer, the term of this patent is extended or adjusted under 35 U.S.C. 154(b) by 31 days.

(21) Appl. No.: 09/899,409

(22) Filed: Jul. 5, 2001

(65) Prior Publication Data

US 2003/0105268 A1 Jun. 5, 2003

(51) Int. Cl.$^7$ .................... C07D 301/03; C07D 301/12; C07D 301/19; C08G 59/02

(52) U.S. Cl. .................... 528/219; 528/212; 528/214; 528/215; 528/217; 549/520; 549/523; 549/531

(58) Field of Search ................ 549/520, 523, 549/531; 548/212, 214, 215, 217, 219

(56) References Cited

U.S. PATENT DOCUMENTS

| | | | |
|---|---|---|---|
| 2,144,612 A | 1/1939 | Britton et al. | |
| 2,714,602 A | 8/1955 | Abbott | |
| 4,314,088 A | 2/1982 | Austin et al. | 568/860 |
| 4,413,151 A | 11/1983 | Michaelson et al. | 568/860 |
| 4,496,779 A | 1/1985 | Myers et al. | 568/860 |
| 4,499,255 A | 2/1985 | Wang et al. | 528/95 |
| 4,507,492 A | 3/1985 | Woo | 560/64 |
| 4,721,798 A | 1/1988 | Mulder | 549/553 |
| 4,740,330 A | 4/1988 | Wang et al. | 568/657 |
| 4,778,863 A | 10/1988 | Wang et al. | 525/507 |
| 4,785,061 A | 11/1988 | Wang et al. | 525/507 |
| 4,871,855 A | 10/1989 | Marko et al. | 546/134 |
| 4,965,364 A | 10/1990 | Marko et al. | 546/134 |
| 5,028,686 A | 7/1991 | Liao et al. | 528/92 |
| 5,126,494 A | 6/1992 | Gilheany et al. | 568/807 |
| 5,227,543 A | 7/1993 | Sharpless et al. | 568/860 |
| 5,260,461 A | 11/1993 | Hartung et al. | 549/447 |
| 5,516,929 A | 5/1996 | Sharpless et al. | 560/38 |
| 5,578,740 A | 11/1996 | Au et al. | 549/525 |
| 6,001,945 A | 12/1999 | Decker et al. | 528/26 |
| 6,005,063 A | 12/1999 | Van Doorn et al. | 528/86 |
| 6,087,513 A | 7/2000 | Liao et al. | 549/524 |
| 6,100,412 A | 8/2000 | Thiele et al. | 549/523 |
| 6,534,621 B2 * | 3/2003 | Boriack et al. | 528/87 |

FOREIGN PATENT DOCUMENTS

| | | |
|---|---|---|
| EP | 0 077 201 A2 | 4/1983 |
| EP | 0 970 951 A1 | 1/2000 |
| WO | WO 92/20677 | 11/1992 |
| WO | WO 98/35927 | 8/1998 |
| WO | WO 99/09020 | 2/1999 |

OTHER PUBLICATIONS

Chemical abstracts accession No. 1991:206710 for the Tetrahedron: Asymmetry article by Rao et al. (1990), vol. 1, No. 10, pp. 697–698.*

Chemical abstracts accession No. 2001:55239 for Japanese Patent No. 2001–17863, Kawamura Institute of Chemical Researc Japan, Jan. 2001.*

Lee et al., "Handbook of Epoxy Resins", Mc–Graw Hill Book Co., New York, NY, pp. 2–3 to 2–4 (1982).

Leeman et al., "Glycidol Properties, Reaction, Applications", New York, NY, pp. 48–52 (1981).

Wasserman, et al, "Retention of Configuration in the Opening of cis– and trans–Dypone Oxides", Journal of the American Chemical Society, 78, pp. 1726 (1956).

Abstract of WO 00/64848, "Method for the Dihydroxylation of Olefins Using Transition–Metal Catalysts" (Nov. 2, 2000).

Murray, et al., "Olefin Epoxidations Using the Dicyclohexylcarbondiimide–$H_2O_2$ System", Journal of Organic Chemistry, 63, pp. 1730–1731,(1998).

Brink, et al., "Selenium Catalysed Oxidations with Aqueous Hydrogen Peroxide", Journal of Chemical Society Perkin, pp. 224–228 (2001).

Murray, "Dioxiranes", Chemical Reviews, 89, pp. 1187–1201 (1989).

Abstract of WO 00/64844, "Method for the Asymmetric Dihydroxylation of Olefins, Using Osmium Catalysts" (Nov. 2, 2000).

Boehlow, et al., "Optical Resolution of Amine N–Oxide by Diastereoisomeric Complex Formation with Optically Active Host Compound", Tetrahedron Letters, 39, pp. 1839–1842 (1989).

Neimann, et al., "A New Non–Metal Heterogeneous Catalyst for the Activation of Hydrogen Peroxide", Chemical Communications, 5, pp. 487–488 (2001).

Shing, et al., Angewandte Chemical, 106, pp. 2408–2409 (1994).

Beller, et al., "Diols via Catalytic Dihydroxylation," Appl. Homogeous Catal. Organomet. Compd., 2, pp. 1009–1010 (1996).

Marko, et al., "Dihydroxylation of Carbon–Carbon Double Bonds", Comprehensive Asymmetric Catalysis, I–III,pp. 713–787 (1999).

Shing, et al., "Ruthenium–Catalyzed cis–Dihydroxylation of AlkenesL Scope and Limitations", Chemical European Journal, 2, pp. 50–57 (1996).

(List continued on next page.)

Primary Examiner—Robert E. L. Sellers

(57) ABSTRACT

A process for manufacturing an α-dihydroxy derivative from an aryl allyl ether wherein such α-dihydroxy derivative can be used to prepare an α-halohydrin intermediate and an epoxy resin prepared therefrom including epoxidizing an α-halohydrin intermediate produced from a halide substitution of an α-dihydroxy derivative which has been obtained by a dihydroxylation reaction of an aryl allyl ether in the presence of an oxidant or in the presence of an oxidant and a catalyst.

92 Claims, No Drawings

OTHER PUBLICATIONS

Johnson, et al., "Catalytic Asymmetric DihydroxylatoinDiscovery and Development", Catalytic Asymmetric Synthesis, Second Edition, pp. 357–398 (2000).

Organic Syntheses Collection, VI, p. 342–348 (1988).

Pini, et al., "Heterogeneous Transition Metal Catalysts", Chim. Ind. (Milan), 81, pp. 189–199 (1999).

Bolm, et al. "Asymmetric Dihydroxylations using Immobolized Alkaloids with an Anthraquinone Core", Synlett, 1, pp. 93–95 (2001).

Van Vliet, et al., "Fluorinated Alcohols: Effective Solvents for Uncatalysed Epoxidations with Aqueous Hydrogen Peroxide", Synlett, 2, pp. 248–250 (2001).

Wirth, "Oxygen and Osmium–A New Alliance for Dihydroxylation?", Angewandte Chemie International Edition, 2, pp. 334–335 (2000).

Bhaumik, et al., "Selective Dihydroxylation over Titanium Silicate Molecular Sieves", Journal of Catalysis, 176, pp. 305–309 (1998).

Mehltretter, et al., "An Improved Version of the Sharpless Asymmetric Dihydroxylation", Tetrahedron Letters, 41, pp. 8083–8087 (2000).

Sharpless, et al., "The Osmium–Catalyzed Asymmetric Dihydroxylation: A New Ligand Class and a Process Improvement", Journal of Organic Chemistry, 10, pp. 2768–2771 (1992).

Kolb, et al., "Catalytic Asymmetric Dihydroxylation", Chemical Reviews, 94, pp. 2483 (1994).

Han, et al., "Soluble Polymer–Bound Ligand–Accelerated Catalysis: Asymmetric Dixydroxylation", Journal of American Chemical Society, 118, pp. 7632–7633 (1996).

Salvadori, et al., "Insoluble Poykmer–Bound (IPB) Approach to the Catalytic Asymmetric Dihydroxylation of Alkenes" Synlett, 8, pp. 1181–1190 (1999).

Severeyns, et al., "A Heterogeneous cis–Dihydroxyation Catalyst with Stable, Site–Isolated Osium–Diolate Reaction Centers", Angewandte Chemie International Edition, 40, pp. 586–589 (2001).

Kobayashi, et al., "Datalytic Asymmetric Dihydroxylation of Olefins Using a Recoverable and Reusable Polymer–Supported Osmium Catalyst", Journal of American Chemical Society, 121, pp. 11229–11230 (1999).

De Vos, et al., "Highly Selective Epoxidation of Alkenes and Styrenes with $H_2O_2$ and Manganese Complexes of the Cyclic Triamine 1,4,7–trimethyl–1,4,7–triazacyclononane", Chemical Communications, pp. 917–918 (1996).

Koek, et al., "Synthesis and Properties of Hydrophobic $[Mn^{IV_2} (\mu-O)_3 (L)_2]^{2+}$ Complexes, Derived from Alkyl Substituted 1,4,7–triazacyclononane Ligands", Inorganica Chimica, 295, pp. 189–199 (1999).

Fatiadi, "The Classical Permanganate Ion: Still a Novel Oxidant in Organic Chemistry" Synthesis, pp. 85, (1987).

Pietikainen, "Asymmetric Mn (III)–salen Catalyzed Epoxidation of Unfunctionalized Alkenes with in situ Generated Peroxycarboxylic Acids", Journal of Molecular Catalysis, 165, pp. 73–79 (2001).

De Vos, et al., "Selective Alkene Oxidation with $H_2O_2$ and a Heterogenized Mn Catalyst: Epoxidation and a New Entryt to Vicinal cis–Diols", Angewandte Chemie International Edition, 38, pp. 980–983, (1999).

Knops–Gerrits, et al., "Oxidation Catalysis with Semi–Inorganic Zeolite–based Mn Catalysts", Journal of Molecular Catalysis A: Chemical, 117, pp. 57–70, (1997).

Sutra, et al., "Preparation of MCM–41 Type Silica–Bound Manganese (III) Schiff–base Complexes", Chemical Communications, pp. 2485–2486 (1996).

Romao, et al., "Rhenium (VII) Oxo and Imido Complexes: Synthesis, Structures, and Applications", Chemical Review, 97, pp. 3197–3246 (1997).

Herrmann, et al., "Organorhenium Oxides", Accounts of Chemical Research, 30, pp. 169–180 (1997).

Owens, et al., "Rhenium Oxo Complexes in Catalytic Oxidations", Catalysis Today, 55, pp. 317–363 (2000).

Herrmann, et al., "Methyltrioxorhenium as Catalyst for Olefin Oxidation", Angewandte Chemie International Edition English, 30, pp. 1638–1643 (1991).

Pietsch, et al., "$LreO_3$ Epoxidizes, cis–Dihydroxylates, and Cleaves Alkenes as Well as Alkenylates Aldehydes: Toward an Understanding of Why", Organometallics, 17, pp. 2716–2719 (1998).

Adam, et al., "Methyltrioxorhenium (VII)–Catalyzed Epoxidation of Alkenes with the Urea/Hydrogen Peroxide Adduct", Angewandte Chemie International Edition English, 35, pp. 533–535 (1996).

Al–Ajlouni, et al., "Kinetics and Mechanism of the Epoxidation of Alkyl–Substituted Alkenes by Hydrogen Peroxide, Catalyzed by Methylrhenium Trioxide", Journal of Organic Chemistry, 61, pp. 3969–3976 (1996).

Tan, et al., "Kinetics and Mechanism of the Dihydroxylation and Epoxidation of Conjugated Dienes with Hydrogen Peroxide Catalyzed by Methylrehenium Trioxide", Inorganic Chemistry, 37, pp. 467–472 (1998).

Shing, et al., "Practical and Rapid Vicinal Hydroxylation of Alkenes by Catalytic Ruthenium Tetraoxide", Angewandte Chemie International Edition English, 33, pp. 2312 (1994).

Shing, et al., "Solvent Effect of Ruthenium Catalyzed Dihydroxylation", Tetrahedron Letters, 40, pp. 2179–2180 (1999).

Bergstad, et al., "A New Coupled Catalytic System for Dihydroxylation of Olefins by $H_2O_2$", Journal of American Chemical Society, 121, pp. 10424–10425 (1999).

Ell, et al., "Vanadyl Acetylacetonate as Peroxide Activator in Osmium–Catalyzed Dihydroxylation of Olefins by Hydrogen Peroxide", Tetrahedron Letters, 42, pp. 2569–2571 (2001).

Li, et al. "Catalytic Asymmetric Dihydroxylation of Gold Colloids Functionalized with Self–Assembled Monolayers", Langmuir, 15, pp. 4957–4959 (1999).

Augustine, "Industrial Uses of Catalytic Oxidation and the Direct Oxidation of Olefins to Glycols", Catalysis of Organic Reactions, pp. 269–278 (1985).

Dobler, et al., "Atom–Efficient Oxidation of Alkenes with Molecular Oxygen: Synthesis of Diols", Angewandte Chemie International Edition, 38, pp. 3026–3028 (1999).

Ell, et al., "Vanadyl Acetylacetonate as Peroxide Activator in Osmium–Catalyzed Dihydroxylation of Olefins by Hydrogen Peroxide", Tetrahedron Letters, 42, pp. 2569–2571 (2001).

Wirth, et al. "Oxygen and Osmium–A New Alliance for Dihydroxylations", Angewandte Chemie International Edition., 39, pp. 334–335 (2000).

Dobler, et al., "Osmium–Catalyzed Dihydroxylation of Olefins Using Dioxygen or Air as the Terminal Oxidant", Journal of the American Chemical Society, 122, pp. 10289–10297 (2000).

\* cited by examiner

PROCESS FOR MANUFACTURING AN ALPHA-DIHYDROXY DERIVATIVE AND EPOXY RESINS PREPARED THEREFROM

BACKGROUND OF THE INVENTION

The present invention relates to a process for manufacturing an α-dihydroxy derivative from an aryl allyl ether and converting such α-dihydroxy derivative to an epoxy resin. The α-dihydroxy derivative may optionally be used to produce an α-halohydrin intermediate which, in turn, is used to make an epoxy resin. For example, the process of the present invention is useful for manufacturing a bisphenol A (bis A) epoxy resin.

In a well-known industrial process for producing epoxy resins on a large commercial scale, in a first step, an α-halohydrin, as a reactive intermediate, is made by reacting an active hydrogen-containing compound such as an alcohol, a phenol, a carboxylic acid or an amine with an epoxide-containing epihalohydrin, such as epichlorohydrin (ECH) or epibromohydrin. In this first step, the epoxide moiety of the epihalohydrin is consumed in the formation of the α-halohydrin moiety. Then, in a second step, the α-halohydrin moiety is converted back into an epoxide moiety of a glycidyl ether, glycidyl ester, or glycidyl amine under basic reaction conditions.

The most widely made and particularly useful epoxy resin is bis A epoxy resin which is made by the coupling reaction of bis A and ECH through the epoxy moiety of ECH to form the bis(α-chlorohydrin) intermediate in a first step. Then, in a dehydrochlorination reaction with base in which an epoxide moiety is reformed, as a second step, the bis A bis(α-chlorohydrin) intermediate is converted to the bis A diglycidyl ether epoxy resin. Such a two-step process for making an epoxy resin is described by H. Lee and K. Neville in "Handbook of Epoxy Resins", McGraw-Hill Book Co., New York, N.Y., 1982, Reissue, 2–3 to 2–4. This process is shown in the following reaction sequence, Reaction Sequence (I). More specifically, Reaction Sequence (I) shows a process chemistry scheme for a two-step, industrial manufacture of bis A epoxy resin via the reaction of bis A and ECH to make a chlorohydrin intermediate.

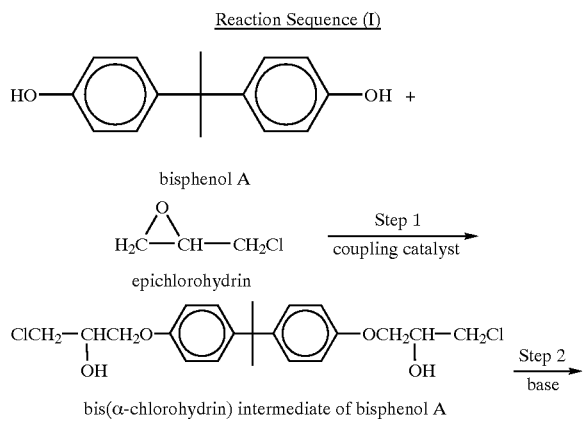

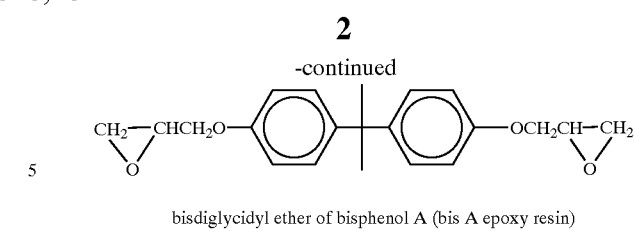

bisdiglycidyl ether of bisphenol A (bis A epoxy resin)

The above two-step process of coupling bis A and ECH by reaction at the epoxide ring followed by epoxide ring-forming dehydrochlorination has also been combined into a single-step reaction, wherein the bis(α-chlorohydrin) intermediate of bis A is generated in situ and converted into an epoxy simultaneously. Such a single-step process for making bis A epoxy resin is described in U.S. Pat. Nos. 4,499,255; 4,778,863; and 5,028,686.

Another method to generate α-chlorohydrins, as reactive intermeditates, that does not consume an epoxide moeity of any of the reactants, is described in U.S. Pat. No. 2,144,612 in which glycerol, which is an α-dihydroxy derivative, is converted into an α-chlorohydrin by reaction with anhydrous hydrogen chloride (HCl) in the presence of a catalytic amount of acetic acid (AcOH). U.S. Pat. No. 2,144,612 describes a process that is shown in the following reaction sequence, Reaction Sequence (II), for making glycerol dichlorohydrin, a precursor for epichlorohydrin from the α-dihydroxy derivative glycerol. More specifically, Reaction Sequence (II) shows chemistry for epichlorohydrin synthesis via the reaction of glycerol with hydrogen chloride and acetic acid to make glycerol dichlorohydrin.

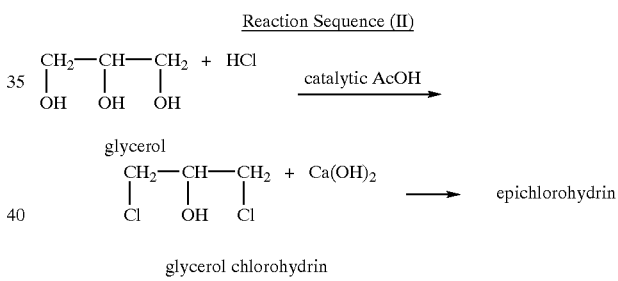

Although ECH is an important commercial product for making α-chlorohydrin intermediates, and particularly for making the bis A bis(α-chlorohydrin) intermediate precursors of bis A epoxy resin, ECH provides a chlorine-intensive route to producing epoxy resins. In the predominate commercial process for making ECH, ECH is made from allyl chloride, which in turn, is made from thermal chlorination of propylene using chlorine gas, a process that produces chlorinated by-products. Generally, chlorinated by-products are treated as waste material.

Additionally, a large amount of water is used when converting allyl chloride into an α-chlorohydrin intermediate and then converting the α-chlorohydrin to ECH, and this water must eventually also be treated as waste. Therefore, from an environmental standpoint, there is a desire to reduce the consumption of chlorine and to reduce the generation of chlorinated by-products and waste water in the production of epoxy resin.

In addition, epoxy resins made from ECH by either of the previously described two-step or single-step processes, may have a high organic chloride content which may be deemed as undesirable in some applications, for example, in electronic applications.

It is therefore desired to provide a non-epichlorohydrin process for making epoxy resins such as bis A epoxy resin. That is, it is desired to provide an alternative epoxy resin route, i.e., an alternative process without using ECH for manufacturing epoxy resins.

One non-epichlorohydrin process for manufacturing epoxy resins is described in U.S. Pat. No. 6,001,945. In the process of U.S. Pat. No. 6,001,945, the epoxide moeity of the reactant glycidol is coupled with bis A to produce an α-dihydroxy derivative, which is subsequently converted to an α-chlorohydrin via reaction with hydrogen chloride and a catalytic amount of acetic acid via the process described in U.S. Pat. No. 2,144,612. Glycidol is known to be a highly toxic and thermally unstable material tending to explosively self-polymerize. At low temperatures, such as 70° C., glycidol is unstable and the loss of epoxide content of glycidol is significant. Glycidol self-polymerization diminishes glycidol selectivity and product yield in its reactions, and the glycidol self-polymerization products complicate separation and purification of the desired reaction product. These undesirable properties of glycidol are described in detail by A. Kleemann and R. Wagner in "Glycidol Properties, Reactions, Applications", Dr. Alfred Huthig Verlag, New York, N.Y., 1981, pp. 48–52. Thus, it is also desirable to develop processes that can manufacture α-halohydrin intermediates as precursors for manufacturing epoxy resins that do not require glycidol as a reactant.

U.S. Patent Application Serial No. 60/205,366 (a provisional application of Ser. No. 09/852,355, U.S. Pat. No. 6,534,621) entitled "Process for Manufacturing a Halohydrin Intermediate and Epoxy Resins Prepared Therefrom," filed by Boriack et al., May 18, 2000, discloses a process for manufacturing an α-halohydrin intermediate of at least one or more phenols and utilizing such α-halohydrin intermediate of the least one or more phenols to make an epoxy resin such as bis A epoxy resin. The above patent application is an improvement over U.S. Pat. No. 6,001,945 by utilizing a stable glycidyl acetate in the place of a highly unstable glycidol. However, even both processes above, consume the epoxide group of an epoxide-containing raw material to make an intermediate which must be subsequently re-epoxidized.

It is therefore desired to provide a novel, alternative process for manufacturing epoxy resins without the use of glycidol or epichlorohydrin.

SUMMARY OF THE INVENTION

The present invention is a new route to an epoxy resin that is significantly more atom efficient than the currently practiced technology. In conventional routes to epoxy resins that proceed through halohydrin intermediates, greater than two moles of halogen (4 atoms of halogen) are required to produce one equivalent of epoxide group. The route of the present invention does not use chlorine to make the epoxy resin, but instead, uses a hydrogen halide. Thus, in the present invention process, only one mole of hydrogen halide (1 atom of halogen) is required to produce one equivalent of epoxide group.

Also, in conventional processes to make epoxy resins, an epoxide-containing raw material, such as epichlorohydrin, is used to make a non-epoxide-containing intermediate which is subsequently reepoxidized. Such a process that consumes the epoxide group of an epoxide-containing raw material to make a second epoxide-containing compound is not atom efficient, utilizes large amounts of energy because formation of epoxide rings is an energy intensive process, and is more complex than the disclosed process. The present process invention, on the other hand, uses α-dihydroxy derivatives as precursors to make α-halohydrin intermediates for epoxy resins.

One aspect of the present invention is directed to a process for preparing an α-dihydroxy derivative useful for a process for making an α-halohydrin intermediate including oxidizing the carbon—carbon double bond of the allyl groups of an aryl allyl ether compound to form an α-dihydroxy derivative. The process for manufacturing the α-dihydroxy derivative is preferably carried out in the presence of an oxidant alone functioning as the oxidizing agent; or in the presence of an oxidant in combination with a catalyst. Optionally, the oxidation process of the present invention is carried out in the presence of certain additives, co-oxidants, and co-catalysts, or a solvent.

Another aspect of the present invention is directed to a process for preparing an epoxy resin by converting the aforementioned α-dihydroxy derivative to an epoxy resin.

Yet another aspect of the present invention is directed to a process for manufacturing an α-halohydrin intermediate using a halide substitution process to convert the α-dihydroxy derivative described above to the α-halohydrin intermediate. The process is preferably carried out under anhydrous conditions with a hydrogen halide such as hydrogen chloride, hydrogen bromide, or hydrogen iodide, as a reactant; and a carboxylic acid, such as acetic acid, present in a catalytic amount or a carboxylic acid ester, such as 1-methoxy-2-propanol acetate, present in a catalytic amount, or present as a solvent; and optionally, the process is carried out in the presence of a non-carboxylic acid ester solvent.

Still another aspect of the present invention is directed to an alternative, non-epichlorohydrin process for manufacturing an epoxy resin of at least one or more phenols utilizing, as an intermediate product, the α-halohydrin intermediate described above.

DETAILED DESCRIPTION OF THE PREFERRED EMBODIMENTS

The present invention is directed to a new process for preparing a glycidyl ether of a phenol or a mixture of phenols from a corresponding allyl ether of a phenol or mixture of phenols. In particular, the present invention is directed to a new process for preparing bisphenol A diglycidyl ether, a common epoxy resin, without the use of epichlorohydrin. This process is outlined generally in the following reaction sequence, Reaction Sequence (III). More specifically, Reaction Sequence (III) shows a process chemistry scheme for conversion of diallyl ether of bisphenol A to bisphenol A epoxy resin via an α-dihydroxy derivative of bisphenol A.

Reaction Sequence (III)

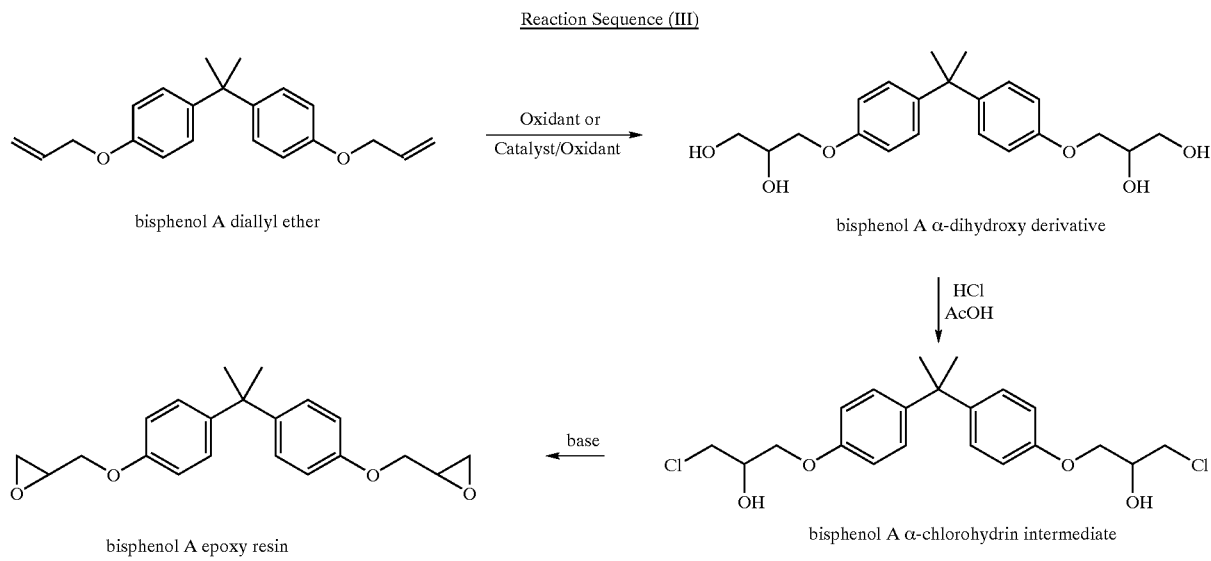

bisphenol A diallyl ether bisphenol A α-dihydroxy derivative bisphenol A epoxy resin bisphenol A α-chlorohydrin intermediate Generally, the present invention includes a process for converting an aryl allyl ether or a mixture of aryl allyl ethers into an α-dihydroxy derivative via a dihydroxylation process by contacting the aryl allyl ether or a mixture of aryl allyl ethers with an oxidant or with an oxidant in combination with a catalyst in an effective amount to form an α-dihydroxy derivative from the aryl allyl ether or mixture of aryl allyl ethers.

The dihyroxylation process of the present invention can be generally described according to the following Scheme I:

Scheme I

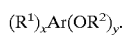

The various elements of the above dihydroxylation process equation of Scheme I are disclosed hereinafter in detail in the subheadings which follow herein.

Aryl Allyl Ethers

The starting material in the dihydroxylation process is an aryl allyl ether or mixture of aryl allyl ethers. "Aryl allyl ether compounds" or "aryl allyl ethers" as used herein means (i) allyl ethers that contain an allyl ether moiety connected directly to an aromatic ring; or (ii) allyl ethers that contain an allyl ether moiety and an aromatic ring, but the allyl ether moiety is not connected directly to the aromatic ring, but instead the allyl ether moiety is linked to the aromatic ring via a linking group such as a polyalkylene oxide group.

In one embodiment of the present invention, the aryl allyl ether or mixture of aryl allyl ethers used in the present invention are those described in U.S. Pat. No. 6,087,513, incorporated herein by reference.

In another embodiment of the present invention, the aryl allyl ether or mixture of aryl allyl ethers useful in the present invention are represented by, but not limited to, the structures of the following Formulas I–V. The following Formula I generically represents a preferred class of aryl allyl ethers used in the present invention:

Formula I $(R^1)_x Ar(OR^2)_y$.

In Formula I, x is from 0 to 750, and y is from 1 to 150. When y is equal to or greater than two, then the aryl allyl ether is a multifunctional allyl ether.

In Formula I, Ar is a moiety containing a mononuclear aromatic ring such as phenyl. Ar may also be a moiety containing multinuclear aromatic rings, such as for example biphenyl, 2,2-diphenyl propane, bisphenylene oxide, tetrakis (1,1,2,2-phenyl)ethane, stilbene, phenol-formaldehyde novolac, cresol-formaldehyde novolac, phenol-dicyclopentadiene novolac and hyper-branched aromatic phenol dendrimers. Ar may also be a moiety containing multinuclear fused aromatic rings such as for example naphthalene, anthracene and naphthalene-formaldehyde novolac. Ar may also be a moiety containing multinuclear fused aromatic rings with one or more heteroatoms such as for example O, N, S, Si, B or P; or any combination of these heteroatoms, such as for example, quinoxaline, thiophene and quinoline. Ar may also be a moiety containing mononuclear or multinuclear aromatic ring(s) fused with a cycloaliphatic ring(s) such as for example indane, 1,2,3,4-tetrahydronaphthalene and fluorene. Ar may also be a moiety containing mononuclear or multinuclear aromatic ring(s) fused with a cycloaliphatic ring(s) containing one or more heteroatoms such as for example O, N, S, Si, B or P; or any combination of these heteroatoms, such as for example, chroman, indoline and thioindane. Ar as described above in Formula I can also be partially or fully fluorinated.

In Formula I, Ar can also be a moiety containing aryl groups in which each aryl group is connected to oligomeric (for example, polymers with less than about 5000 molecular weight average) or high molecular weight (for example, greater than about 5000 molecular weight average) organosiloxane units. The aryl groups are attached directly to the Si atoms of the organosiloxane units, or the aryl groups are indirectly attached to the Si atoms of the organosiloxane units via an organic aliphatic moiety, organic cycloaliphatic moiety, organic aromatic moiety, or any combination thereof. The organic aliphatic, cycloaliphatic, or aromatic moiety should contain no more than 20 carbon atoms. When the Ar moiety contains such oligomeric or high molecular weight organosiloxane units, then y is preferably from 2 to 150.

In Formula I, $R^1$ is a group substituted for a hydrogen atom on the aromatic ring(s) of the Ar moiety. $R^1$ is a halogen atom such as, for example, bromine or chlorine; or a hydrocarbon radical such as an alkyl group, a cycloaliphatic group or aromatic group. $R^1$ is preferably an alkyl group having from 1 to 20 carbon atoms such as, for example methyl, ethyl or propyl; a cycloaliphatic group having from 3 to 20 carbon atoms such as, for example, cyclopentyl or cyclohexyl; an aromatic group having from 6 to 20 carbon atoms such as, for example, phenyl or naphthyl; or any combination thereof. The hydrocarbon radicals above may also contain one or more heteroatoms such as, for example, O, N, S, Si, B, P or any combination of these heteroatoms. An example of a hydrocarbon radical containing an O heteroatom is a methoxy group, an ethoxy group or a polyalkylene oxide group derived from ethylene oxide, propylene oxide, butylene oxide or cyclohexene oxide. $R^1$ as described above in Formula I can be partially or fully fluorinated.

In Formula I, O is an oxygen atom substituted for a hydrogen atom on the aromatic ring(s) of the Ar moiety, and $R^2$ is, for example, a propenyl-containing moiety preferably selected from:

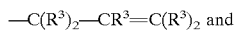

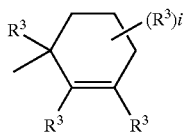

where $R^3$ is hydrogen; or an alkyl group, a cycloaliphatic group or aromatic group; and i is from 0 to 6. $R^3$ is preferably an alkyl group having from 1 to 20 carbon atoms such as, for example, methyl, ethyl or propyl; a cycloaliphatic group having from 3 to 20 carbon atoms such as, for example, cyclopentyl or cyclohexyl; an aromatic group having from 6 to 20 carbon atoms such as, for example, phenyl or naphthyl; or any combination thereof. Each individual $R^3$ may be the same group or may be a different group from each other.

In Formula I, $R^2$ may also be a monoalkylene oxide group or a polyalkylene oxide group derived from, for example, ethylene oxide, propylene oxide, butylene oxide or cyclohexene oxide; wherein each monoalkylene oxide group or each polyalkylene oxide group is terminated with, for example, a propenyl-containing moiety selected from:

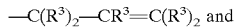

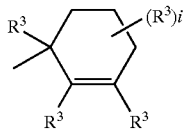

where $R^3$ is as described above.

In one embodiment, when $R^2$ in Formula I above is —$CH_2CH=CH_2$, the ether is an "allyl ether."

In another embodiment, when $R^2$ is —$CH_2C(CH_3)=CH_2$ in Formula I above, the aryl ether is a "methallyl ether."

In yet another embodiment, when $R^2$ in Formula I above is

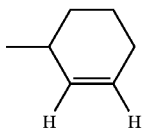

the aryl ether is a "cyclohexen-3-yl ether."

More specific and preferred examples of aryl allyl ethers useful in the present invention are represented by Formulas II–V which follow.

Examples of mononuclear aryl allyl ethers useful in the present invention are represented by the following Formula II:

Formula II

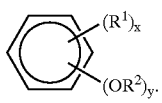

In Formula II, $R^1$, O and $R^2$ have the same meaning as described above with reference to Formula I. In Formula II, x is from 0 to 5 and y is from 1 to 4. Aryl allyl ethers of Formula II, can be, represented by, for example, 2-methyl phenyl allyl ether; 4-methyl phenyl allyl ether; 4-methoxyphenyl allyl ether; 2,6-dimethylphenyl allyl ether; 2,6-diisopropylphenyl allyl ether; 2,6-dibromophenyl allyl ether; 1,2-, 1,3- and 1,4-benzene diallyl ethers; 1,4-, 1,5- and 2,6-naphthalene diallyl ethers; and mixtures thereof.

Other examples of aryl allyl ethers useful in the present invention are binuclear aryl allyl ethers which are represented by the following Formula III:

Formula III

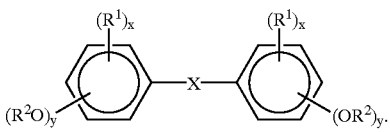

In Formula III, $R^1$, O and $R^2$ have the same meaning as described above with reference to Formula I. In Formula III, each x is from 0 to 4, and each x can be the same or different, and each y is from 1 to 4, and each y can be the same or different.

In Formula III, X may be nil; or X can be a heteroatom with or without substituents thereon to complete its necessary bonding valence; the heteroatom is preferably selected from O, N, S, Si, B or P, or any combination of two or more of the above heteroatoms. X can also be, for example, —C(O)—, —S(O₂)—, —C(O)NH—, or —P(O)Ar—. X can also be, for example an organic aliphatic moiety, with or without heteroatoms, such as, for example, oxydimethylene, methylene, 2,2-isopropylidene, isobutylene, or —$CR^3$=CH—, where $R^3$ is as defined with reference to Formula I above. X can also be, for example, a cycloaliphatic group, with or without heteroatoms, such as, for example, a cycloaliphatic ring with greater than 3 carbon atoms; or an aromatic group, with or without heteroatoms; or any combination thereof, preferably with no more than 60 carbon atoms. X as described above in Formula III can be partially or fully fluorinated, such as, for example, 2,2-perfluoroisopropylidene.

Precursors useful for making the aryl allyl ethers of Formula III include, for example, 4,4'-dihydroxybiphenyl;

3,3',5,5'-tetramethyl-4,4'-dihydroxybiphenyl; 3,3',5,5'-tetramethyl-2,2',6,6'-tetrabromo-4,4'-dihydroxybiphenyl; bis(4-hydroxyphenyl)methane; bis(4-hydroxyphenyl) sulfone; 2,2-bis(3,5-dibromo-4-hydroxyphenyl) isopropylidene; 2,2-bis(4-hydroxyphenyl)isopropylidene; bisphenol K; 9,9-bis(4-hydroxyphenyl)fluorene; 4,4'-dihydroxy-α-methylstilbene; and 1,3-bis(4-hydroxylphenyl) adamantane.

Other examples of aryl allyl ethers useful in the present invention are multinuclear aryl allyl ethers which are represented by the following Formula IV:

Formula IV

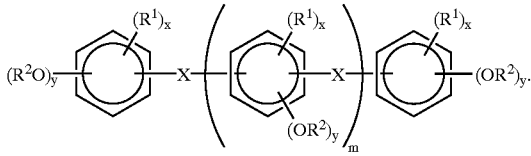

In Formula IV, $R^1$, O, $R^2$ and x have the same meaning as described above with reference to Formula III. In Formula IV, each x is from 0 to 4, and each x can be the same or different, and each y is from 1 to 4, and each y can be the same or different. In Formula IV, m is from 0.001 to 10.

Precursors useful for making the aryl allyl ethers of Formula IV include, for example, phenol-formaldehyde novolac (functionality greater than 2); o-cresol-formaldehyde novolac (functionality greater than 2); phenol-dicyclopentadienyl novolac (functionality greater than 2); and naphthol-formaldehyde novolac (functionality greater than 2).

Other examples of aryl allyl ethers useful in the present invention are multi-nuclear aryl allyl ethers which are represented by the following Formula V:

Formula V

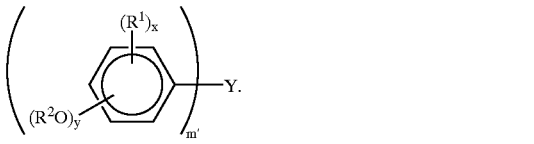

In Formula V, $R^1$, O and $R^2$ have the same meaning as described previously with reference to Formula I. In Formula V, each x is from 0 to 4, and each x can be the same or different, and each y is from 1 to 4, and each y can be the same or different.

In Formula V, Y is an organic aliphatic moiety, with or without heteroatoms such as, for example, O, N, S, Si, B or P, or any combination of two or more of the above heteroatoms, wherein the aliphatic moiety has from 1 to 20 carbon atoms, such as, for example, methine; a cycloaliphatic moiety, with or without heteroatoms, having from 3 to 20 carbon atoms, such as, for example, cyclohexane tri-yl; an aromatic moiety, with or without heteroatoms, such as, for example, benzenetriyl, naphthylenetriyl, fluorenetriyl; or any combination thereof, with no more than about 20 carbon atoms. Y as described above in Formula V can be partially or fully fluorinated, such as, for example fluoromethine.

In Formula V, m' is generally 3 or 4. However, Y may also be an oligomeric (for example, less than about 5000 molecular weight average) organosiloxane unit or high molecular weight (for example, greater than about 5000 molecular weight average) organosiloxane unit. In which case, the aryl groups are attached to the Si atoms of the organosiloxane unit directly or through an organic aliphatic, cycloaliphatic, aromatic group, or any combination thereof, with no more than about 20 carbon atoms. When Y is an oligomeric or high molecular weight organosiloxane unit, m' in Formula V is preferably from 1 to 150.

Precursors useful for making the aryl allyl ethers of Formula V include, for example, tris(4-hydroxyphenyl) methane; tris(3,5-dimethyl-4-hydroxyphenyl)methane; and 1,1,2,2'-tetrakis(4-hydroxyphenyl)ethane.

Even more particularly, the process of the present invention utilizes aryl diallyl ethers or aryl multifunctional allyl ethers. An example of an aryl diallyl ether useful in the present invention includes the diallyl ether of bisphenol A.

Typically, the aryl allyl ethers used in the present invention are made from phenolic compounds or hydroxy-containing aromatic compounds.

Phenolic Compounds

The hydroxy moiety of the hydroxy-containing aromatic compound can be directly attached to the aromatic ring of the hydroxy-containing aromatic compound, in which case it is a phenolic compound; or the hydroxy moiety may not be connected directly to the aromatic ring, but instead the hydroxy moiety may be linked to the aromatic ring via a linking group such as a polyalkylene oxide group.

The phenolic compound useful in the above process for synthesizing the aryl allyl ether, is represented by, but not limited to, any one of the structures of the following Formulas VI–X. A preferred class of phenolic compounds useful in the present invention for reacting with an allylating agent to make an α-dihydroxy derivative is generically represented by the following Formula VI:

Formula VI

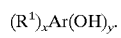

$(R^1)_x Ar(OH)_y$.

In Formula VI, x, y, Ar and $R^1$, are as defined previously for Formula I, and OH is a hydroxyl group substituted for a hydrogen atom on the aromatic ring(s) of the Ar moiety.

More specific and preferred examples of phenolic compounds useful in the present invention are represented by Formulas VII–X, separately or as mixtures of two or more phenolic compounds of Formulas VII–X which follow.

Examples of mononuclear phenolic compounds useful in the present invention are represented by the following Formula VII:

Formula VII

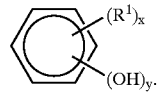

In Formula VII, x, y and $R^1$ have the same meaning as described above with reference to Formula II, and OH has the same meaning as described above with reference to Formula VI.

Included among the compounds represented by Formula VII are, for example, 2-methylphenol; 4-methylphenol; 4-methoxyphenol; 2,6-dimethylphenol; 2,6-diisopropylphenol; 2,6-dibromophenol; 1,2-, 1,3- and 1,4-dihydroxybenzene; 1,4-, 1,5- and 2,6-dihydroxy naphthalene; and mixtures thereof.

Other examples of phenolic compounds useful in the present invention are binuclear phenolic compounds which are represented by the following Formula VIII:

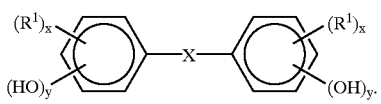

Formula VIII

In Formula VIII, x, y, $R^1$ and X have the same meaning as described above with reference to Formula III, and OH has the same meaning as described above with reference to Formula VI.

Included among the phenolic compounds represented by Formula VIII are, for example, 4,4'(3,3',5,5'-tetramethyl) bisphenol A; 4,4'(3,3'5,5'-tetramethyl-2,2',6,6'-tetrabromo) bisphenol A; 4,4'(3,3'5,5'-tetramethyl)bisphenol F; 4,4'-dihydroxybiphenyl; 3,3',5,5'-tetramethyl-4,4'-dihydroxybiphenyl; 3,3',5,5'-tetramethyl-2,2',6,6'-tetrabromo-4,4'-dihydroxybiphenyl; bis(4-hydroxyphenyl) methane; bis(4-hydroxyphenyl)sulfone; 2,2-bis(3,5-dibromo-4-hydroxyphenyl)isopropylidene; 2,2-bis(4-hydroxyphenyl)isopropylidene; 4,4'-bisphenol K; 9,9-bis(4-hydroxyphenyl)fluorene; 4,4'-dihydroxy-α-methylstilbene; 1,3-bis(4-hydroxylphenyl)adamantane; and mixtures thereof.

Other examples of phenolic compounds useful in the present invention are multinuclear phenolic compounds which are represented by the following Formula IX:

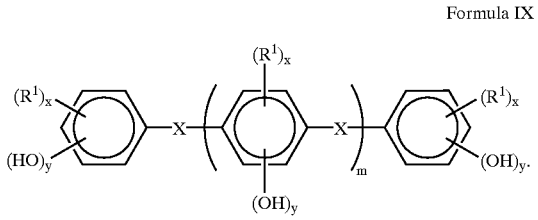

Formula IX

In Formula IX, x, y, $R^1$, X and m have the same meaning as described above with reference to Formula IV, and OH has the same meaning as described above with reference to Formula VI.

Included among the phenolic compounds represented by Formula IX are, for example, phenol-formaldehyde novolac (functionality greater than 2); o-cresol-formaldehyde novolac (functionality greater than 2); phenol-dicyclopentadienyl novolac (functionality greater than 2); naphthol-formaldehyde novolac (functionality greater than 2); and mixtures thereof.

Other examples of phenolic compounds useful in the present invention are multi-nuclear phenolic compounds which are represented by the following Formula X:

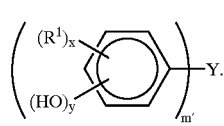

Formula X

In Formula X, x, y, $R^1$, Y and m' have the same meaning as described above with reference to Formula V, and OH has the same meaning as described above with reference to Formula VI.

Included among the phenolic compounds represented by Formula X are, for example, tris(4-hydroxyphenyl)methane; tris (3,5-dimethyl-4-hydroxyphenyl)methane; 1,1,2,2-tetrakis (4-hydroxyphenyl)ethane; and mixtures thereof.

Preferred phenolic compounds of the present invention include more specifically, the phenols, such as for example, 1,3-dihydroxybenzene; 1,4-dihydroxybenzene; 1,5-dihydroxynaphthalene; 2, 6-dihydroxynaphthalene; 4,4'-dihydroxybiphenyl; 3,3',5,5'-tetramethyl-4,4'-dihydroxybiphenyl; 3,3',5,5'-tetramethyl-2,2',6,6'-tetrabromo-4,4'-dihydroxybiphenyl; bis(4-hydroxyphenyl) methane; 4,4'-bis(2,6-dibromophenol)isopropylidene; 2,2-bis(4-hydroxyphenyl)isopropylidene; phenol-formaldehyde novolac (functionality>2); o-cresol-formaldehyde novolac (functionality>2); phenol-dicyclopentadienyl novolac (functionality>2); naphthol-formaldehyde novolac (functionality>2); tris(4-hydroxyphenyl) methane; 1,1,2,2-tetrakis(4-hydroxyphenyl)ethane; and mixtures thereof.

The phenols or mixtures of phenols described above are used to make the aryl allyl ethers useful in the present invention. The aryl allyl ethers useful in the present invention may be synthesized by reacting, for example, an allylating agent such as for example, allyl chloride, allyl bromide, methallyl chloride, allyl acetate, allyl alcohol or allyl carbonate with a phenol, a mixture of phenols, or a hydroxy-containing aromatic compound. The reaction between the phenol, mixture of phenols or hydroxy-containing aromatic compound, and the alylating agent may be done with or without catalysts or with or without bases, for example, as disclosed in U.S. Pat. Nos. 5,578,740; 4,740,330 and 4,507,492; incorporated herein by reference.

Typically, the α-dihydroxy derivatives used in the present invention are made from the aryl allyl ethers prepared above. The α-dihydroxy derivatives, in turn, are useful in manufacturing epoxy resins of the present invention.

α-Dihydroxy Derivatives

The preferred α-dihydroxy derivatives useful in the present invention are represented for example by, but not limited to, the structures of the following Formulas XI–XV. A preferred class of α-dihydroxy derivatives used in the present invention is generically represented for example by the following Formula XI:

Formula XI

In Formula XI, x, y, Ar, O and $R^1$ are as defined in Formula I.

In Formula XI, $R^4$ is an α-dihydroxy propyl-containing moiety preferably selected from:

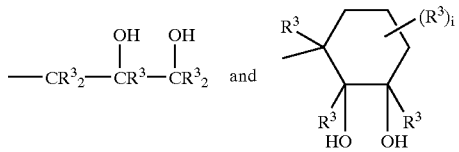

wherein $R^3$ and i are defined previously for Formula I and OH is a hydroxyl group.

In one embodiment, when $R^4$ in Formula XI above is the following structure:

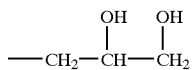

the α-dihydroxy derivative is an α-dihydroxy derivative of an aryl "allyl ether."

In another embodiment, when $R^4$ in Formula XI above is the following structure:

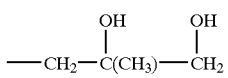

the α-dihydroxy derivative is an α-dihydroxy derivative of an aryl "methallyl ether."

In yet another embodiment, when $R^4$ in Formula XI above is the following structure:

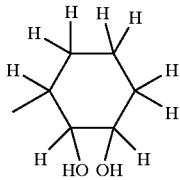

the α-dihydroxy derivative is an α-dihydroxy derivative of an aryl "cyclohexene-3-yl ether."

More specific and preferred examples of α-dihydroxy derivatives useful in the present invention are represented by Formulas XII–XV separately or as mixtures of two or more α-dihydroxy derivatives of Formulas XII–XV which follow.

Examples of mononuclear aromatic α-dihydroxy derivatives useful in the present invention are represented by the following Formula XII:

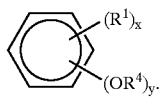

Formula XII

In Formula XII, x, y, O and $R^1$ have the same meaning as described above with reference to Formula II. In Formula XII, $R^4$ has the same meaning as described above with reference to Formula XI. α-Dihydroxy derivatives of Formula XII can be prepared from aromatic hydroxyl group-containing precursors, such as, for example, 2-methylphenol; 4-methylphenol; 4-methoxyphenol; 2,6-dimethylphenol; 2,6-diisopropylphenol; 2,6-dibromophenol; 1,2-, 1,3- and 1,4-dihydroxybenzene; 1,4-, 1,5- and 2,6-dihydroxynaphthalene; or mixtures thereof.

Other examples of α-dihydroxy derivatives useful in the present invention are binuclear aromatic α-dihydroxy derivatives which are represented by the following Formula XIII:

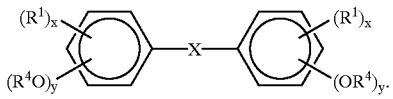

Formula XIII

In Formula XIII, x, y, X, O and $R^1$ have the same meaning as described above with reference to Formula III. In Formula XIII, $R^4$ has the same meaning as described above with reference to Formula XI.

Precursors useful for making the α-dihydroxy derivatives of Formula XIII include, for example, 4,4'-dihydroxybiphenyl; 3,3',5,5'-tetramethyl-4,4'-dihydroxybiphenyl; 3,3',5,5'-tetramethyl-2,2',6,6'-tetrabromo-4,4'-dihydroxybiphenyl; bis(4-hydroxyphenyl)methane; bis(4-hydroxyphenyl)sulfone; 2,2-bis(3,5-dibromo-4-hydroxyphenyl)isopropylidene; 2,2-bis(4-hydroxyphenyl)isopropylidene; bisphenol K; 9,9-bis(4-hydroxyphenyl)fluorene; 4,4'-dihydroxy-α-methylstilbene; 1,3-bis(4-hydroxylphenyl)adamantane; or mixtures thereof.

Other examples of α-dihydroxy derivatives useful in the present invention are multi-nuclear aromatic α-dihydroxy derivatives which are represented by the following Formula XIV:

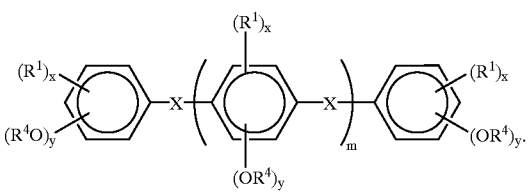

Formula XIV

In Formula XIV, x, y, X, m, O and $R^1$ are as described above for Formula IV. In Formula XIV, $R^4$ has the same meaning as described above with reference to Formula XI.

Precursors useful for making the α-hydroxy ester deivatives of Formula XIV include, for example, phenol-formaldehyde novolac (functionality greater than 2); o-cresol-formaldehyde novolac (functionality greater than 2); phenol-dicyclopentadienyl novolac (functionality greater than 2); naphthol-formaldehyde novolac (functionality greater than 2); or mixtures thereof.

Other examples of α-dihydroxy derivatives useful in the present invention are multi-nuclear aromatic α-dihydroxy derivatives which are represented by the following Formula XV:

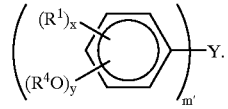

Formula XV

In Formula XV, x, y, Y, m', O and $R^1$ are the same as previously described above for Formula V. In Formula XV, $R^4$ has the same meaning as described previously with reference to Formula XI.

Precursors useful for making the α-dihydroxy derivatives of Formula XV include, for example, tris(4-hydroxyphenyl) methane; tris (3,5-dimethyl-4-hydroxyphenyl)methane; 1,1, 2,2-tetrakis (4-hydroxyphenyl)ethane; or mixtures thereof.

Preferred α-dihydroxy derivatives useful in the present invention include, for example, (2,3-α-dihydroxypropyl) ether of 2-methylphenol; (2,3-α-dihydroxypropyl)ether of 4-methylphenol; (2,3-α-dihydroxypropyl)ether of 4-methoxyphenol; (2,3-α-dihydroxypropyl)ether of 2,6-dimethylphenol; (2,3-α-dihydroxypropyl)ether of 2,6-diisopropylphenol; (2,3-α-dihydroxypropyl)ether of 2,6-dibromophenol; bis(2,3-α-dihydroxypropyl)ether of 1,2-, 1,3- and 1,4-dihydroxybenzene; bis(2,3-α-dihydroxypropyl) ether of 1,4-, 1,5- and 2,6-dihydroxynaphthalene; bis(2,3-α-dihydroxypropyl)ether of 4,4'-(3,3',5,5'-tetramethyl) bisphenol A; bis(2,3-α-dihydroxypropyl)ether of 4,4'-(3,3', 5,5'-tetramethyl-2,2',6,6'-tetrabromo)bisphenol A; bis(2,3-α-dihydroxypropyl)ether of 4,4'-(3,3',5,5'-tetramethyl) bisphenol F; bis(2,3-α-dihydroxypropyl)ether of 4,4'-(3,3'5, 5'-tetramethyl)biphenol; bis(2,3-α-dihydroxypropyl)ether of 4,4'-biphenol; bis(2,3-α-dihydroxypropyl)ether of 4,4'-(3, 3'5,5'-tetramethyl-2,2',6,6'-tetrabromo)biphenol; bis(2,3-α-dihydroxypropyl)ether of 4,4'-bisphenol F; bis(2,3-α-dihydroxypropyl)ether of 4,4'-bisphenol sulfone; bis(2,3-α-dihydroxypropyl)ether of 4,4'-(3,3'5,5'-tetrabromo)

bisphenol A; bis(2,3-α-dihydroxypropyl)ether of 4,4'-bisphenol A; bis(2,3-α-dihydroxypropyl)ether of 4,4'-bisphenol K; bis(2,3-α-dihydroxypropyl)ether of 9,9-bis(4-hydroxyphenyl)fluorene; bis(2,3-α-dihydroxypropyl)ether of 4,4'-dihydroxy-α-methylstilbene; bis(2,3-α-dihydroxypropyl)ether of 1,3-bis(4-hydroxyphenyl)adamantane; (2,3-α-dihydroxypropyl)ether of phenol-formaldehyde novolac (functionality>2); (2,3-1-dihydroxypropyl)ether of o-cresol-formaldehyde novolac (functionality>2); (2,3-α-dihydroxypropyl)ether of phenol-dicyclopentadienyl novolac (functionality>2); (2,3-α-dihydroxypropyl)ether of naphthol-formaldehyde novolac (functionality>2); tris(2,3-α-dihydroxypropyl)ether of trisphenylol methane; tris(2,3-α-dihydroxypropyl)ether of tris(3,5-dimethyl-4-hydroxyphenyl)methane; tetra(2,3-α-dihydroxypropyl)ether of 1,1,2,2-tetraphenylol ethane; and mixtures thereof.

Generally, the present invention includes a process for converting an aryl allyl ether or mixture of two or more aryl allyl ethers into an α-dihydroxy derivative via a dihydroxylation process by contacting the aryl allyl ether or mixture of two or more aryl allyl ethers with an oxidant, or with an oxidant and a catalyst, effective to form an α-dihydroxy derivative from the aryl allyl ether or mixture of two or more aryl allyl ethers.

Dihydroxylation Processes

α-Dihydroxylation of aryl allyl ethers is carried out using either one of two basic processes: (i) a non-catalytic process in which dihydroxylation of the aryl allyl ether is carried out using only an oxidant; or (ii) a catalytic process in which dihydroxylation of the aryl allyl ether is carried out using an oxidant in the presence of a catalyst.

In addition, α-dihydroxylation of aryl allyl ethers to form an α-dihydroxy derivative is carried out either in (i) a direct or (ii) an indirect process.

In the direct α-dihydroxylation process, the allyl groups of the aryl allyl ether are oxidized directly to the α-dihydroxy derivative. The direct α-dihydroxylation process is accomplished by any one of a number of α-dihydroxylation reaction processes well-know to those skilled in the art, such as, for example, by reacting the aryl allyl ether with an oxidizing material or by reacting the aryl allyl ether with an oxidizing material in the presence of a catalyst.

In the indirect α-dihydroxylation process, the allyl groups of the aryl allyl ether are oxidized indirectly to the α-dihydroxy derivative. In the indirect α-dihydroxylation process, the allyl groups of the aryl allyl ether are first oxidized to a transient epoxide intermediate, which may or may not be observed. When the transient epoxide intermediate is not observed it is essentially instantaneously converted in situ into an α-dihydroxy derivative. The indirect α-dihydroxylation process is accomplished by any one of a number α-dihydroxylation reaction processes well-know to those skilled in the art, such as, for example, by reacting the aryl allyl ether with an oxidizing material or by reacting the aryl allyl ether with an oxidizing material in the presence of a catalyst.

The direct and indirect α-dihydroxylation processes are not always clearly distinguishable one from the other, and, in fact, it is sometimes not possible to identify which of these two processes is occurring during an α-dihydroxylation process. Though in the following description of the present invention, the direct and indirect α-dihydroxylation processes are differentiated and described separately. These descriptions should not be taken as definitive since as discussed above the distinction of the direct and indirect dihydroxylation processes are not always obvious from the other.

Non-Catalytic Dihydroxylation Processes

In the non-catalytic α-dihydroxylation process, the allyl groups of the aryl allyl ethers of the present invention are dihydroxylated using only an oxidant.

One category of oxidants, useful in the non-catalytic α-dihydroxylation process may be, for example, aromatic and aliphatic organic peracids, organic peroxyimidic acids, selenic peracids, and dioxiranes.

In one embodiment of the present invention, non-catalytic α-dihydroxylation processes using peracid may be used to form α-dihydroxylation derivatives of aryl allyl ethers in good to excellent yields. Peracids useful in the present invention may include for example, aromatic peracids, such as, for example, m-chloroperbenzoic acid, peroxybenzoic acid, and monoperoxyphthalic acid; aliphatic peracids, such as, for example, peracetic acid (also known as peroxyacetic acid) as described, for example, by C. Y. Curtin, et al., in *J. Amer. Chem. Soc.,* 78, pp. 1726, (1956) and by L. S. Abott in U.S. Pat. No. 2,714,602, both of which are incorporated herein by reference; or peroxyimidic acids, such as the one described by R. Murry in *J. Org. Chem.,* 63, pp. 1730–1731, (1998), incorporated herein by reference.

In another embodiment of the present invention, peracid oxidants may be generated in situ in a non-catalytic dihydroxylation process. For instance, organic nitriles, such as acetonitrile, may be reacted with air, oxygen, hydrogen peroxide, or organic hydroperoxide to form in situ peroxyimidic acids; and carboxylic acids or carboxylic acid anhydrides, such as acetic acid or acetic anyhydride, may be reacted with air, oxygen, hydrogen peroxide, or organic hydroperoxides to form in situ peroxycarboxylic acids. In particular, the peroxycarboxylic acid oxidants can be generated in situ by reaction of air, or oxygen, with the corresponding aliphatic aldehyde, as described in U.S. Pat. No. 4,721,798, which is incorporated herein by reference.

Also, another example of in situ generated peracids are the selenic peracids, such as for example, the selenic peracids generated from diselenides and hydrogen peroxide as described by R. A. Sheldon, et al., in *J. Chem. Soc., Perkin Trans.* 1, pp. 224–228, (2001), which is incorporated herein by reference.

In yet another embodiment of the present invention, organic dioxiranes may be used in non-catalytic α-dihydroxylation processes to form α-dihydroxy derivatives of aryl allyl ethers. Organic dioxiranes useful for the non-catalytic dihydroxylation process, include, for example, dimethyldioxarane as described, for example, by R. Murry in *Chem. Rev.,* 89, pp. 1187–1201, (1989); perfluorodimethyldioxaranes, which may be made from a perfluoroketone and hydrogen peroxide, as described, for example, by R. Sheldon in *Synlett,* (2), pp. 248–250 (2001); and heterogenous or resin-bound in situ formed dioxiranes such as described, for example, by T. R. Boehlow, et al., in *Tetrahedron Letters,* 39, pp. 1839–1842, (1989) and by R. Newmann, et al., in *Chemical Communications,* (5), pp. 487–488, (2001); all of which are incorporated herein by reference.

A second category of oxidants useful in the non-catalytic α-dihydroxylation process, includes oxides of osmium, such as osmium tetroxide ($OSO_4$) When osmium tetroxide is used as an oxidant in the α-dihydroxylation process, it is used in a stoichiometric amount relative to the number of equivalents of allyl ether groups to be dihydroxylated. Thus, in this type of α-dihydroxylation process, osmium is not used as a catalyst but as a stoichiometric reagent.

Other oxidants which may be used in the α-dihydroxylation process of the present invention include, for example, organic N-oxides; persulfates; and oxidizing metal salts, such as $K_3Fe(CN)_6$, or $KIO_4$, and the like.

In a preferred embodiment of the present invention, the ratio of the oxidant used for dihydroxylation of the aryl allyl ether in a non-catalytic dihydroxylation process is preferably in the range of from about 0.6 mole to about 20 moles of oxidant to 1 equivalent of aryl allyl ether. More preferably, the ratio of oxidant used for dihydroxylation of the aryl allyl ether is in the range of from about 1 mole to about 5 moles of oxidant to 1 equivalent of aryl allyl ether. The most preferred ratio for oxidant used for non-catalytic dihydroxylation of the aryl allyl ether is from about 1 mole to about 2.5 moles of oxidant to 1 equivalent of aryl allyl ether. One equivalent of oxidant is theoretically required to oxidize one equivalent of a aryl mono-allyl ether substrate, but it may be desirable to employ an excess of oxidant to optimize conversion to the α-dihydroxy derivative.

Catalytic Dihydroxylation Processes

In catalytic α-dihydroxylation process, the allyl groups of the aryl allyl ethers of the present invention are dihydroxylated catalytically using preferably a transition metal catalyst from the group comprising Group IVA, Group VA, Group VIA, Group VIIA, and Group VIII transition metals or a Group VIB (old IUPAC group notation) element catalyst and an oxidant.

Among the transition metal- or Group VIB element-containing catalysts more preferably useful in the present invention are the catalysts having transition metals or Group VIB elements selected from the group comprising Os, Mn, Re, Ru, W, Cr, Mo, V, Ti, Se, Te or mixtures thereof.

The catalysts useful for dihydroxylation of allyl ether groups of aryl allyl ether compounds are classified as either (i) direct α-dihydroxylation catalysts or (ii) indirect α-dihydroxylation catalysts. The dihydroxylation catalyst is classified as a direct α-dihydroxylation catalyst or as an indirect α-dihydroxylation catalyst dependent on the chemical mechanism through which the dihydroxylation catalyst converts the aryl allyl ether to the α-dihydroxy derivative as discussed previously above.

Catalytic, direct α-dihydroxylation of allyl ether groups of aryl allyl ether compounds is done by oxidizing the allyl ether groups directly to yield the α-dihydroxy derivative. In one embodiment of the present invention, the most preferred transition metal complexes or compounds useful as direct α-dihydroxylation catalysts may be selected from the group of transition metals comprising, Os, Mn, Re, Ru or mixtures thereof.

In another embodiment of the present invention, the most preferred transition metal catalysts useful as α-dihydroxylation catalysts are compounds or complexes of osmium. The general use of osmium-based dihydroxylation catalysts is well-known to those skilled in the art and is reviewed comprehensively by K. B. Sharpless, et al., in "Catalytic Asymmetric Synthesis", pp. 357–398, Second Edition, Edited by Iwao Ojima, Wiely-VCH, 2000; and by I. E. Marko, et al., "Dihydroxylation of Carbon—Carbon Double Bonds", pp. 713–787 in Compr. Asymmetric Catal. I-III, 2, Edited by E. N. Jacobsen, et al., Springer-Verlag, Berlin, Germany (1999), both of which are incorporated herein by reference.

The use of homogeneous osmium-based dihydroxylation catalysts containing asymetric ligands is well-known to those skilled in the art and is described in U.S. Pat. Nos. 4,496,779; 4,871,855; 4,965,364; 5,126,494; 5,227,543; 5,260,461; and 5,516,929; and WO Patent No. 92/20677; all of which are incorporated herein by reference.

It is also known in the art to use homogeneous, recyclable osmium-based dihydroxylation catalysts which are bound to basic ligands, such as alkaloids. Such homogeneous, recyclable osmium-based dihydroxylation catalysts are homogeneous during the α-dihydroxylation process but are precipitated from the reaction mixture at the end of the reaction, as described by K. D. Janda, et al., in *J. Am. Chem. Soc.*, 118(32), pp. 7632–7633 (1996); in PCT Int. Appl.; and in WO 9835927 A1; all of which are incorporated herein by reference.

The use of recyclable, heterogeneous osmium-based dihydroxylation catalysts is well-known to those skilled in the art and is comprehensively reviewed by D. Pini, et al., in *Chim. Ind. (Milan)*, 81(2), pp. 189–199, (1999). In addition, the use of heterogeneous, alkaloid supported polymeric osmium-based dihydroxylation catalysts is described by C. Bolm, et al., in *Synlett*, No. 1, pp. 93–95, (2001); and by P. Salvadori, et al., in *Synlett*, No. 8, pp. 1181–1190, (1999). It is also known to use heterogeneous, polymer-supported or immobilized osmium salts for catalytic dihydroxylations as described by P. A. Jacobs, et al., in *Angew. Chem. Int. Ed.*, 40, No. 3, pp. 586–589 (2001); and by S. Kobayashi, et al., in *J. Am. Chem. Soc.*, 121(48), pp. 11229–11230, (1999). All of the above-mentioned references are incorporated herein by reference.

In another embodiment of the present invention, the transition metal catalysts useful as α-dihydroxylation catalysts are compounds or complexes of manganese. The use of homogeneous manganese-based dihydroxylation catalysts is well-known to those skilled in the art and is described, for instance, by D. E. J. E. De Vos, et al., in European Patent EP 98-202315 and in *Chem. Commun.*, pp. 917–918, (1996); by J. H. Kek, et al., *Inorganica Chimica Acta*, 295, pp. 189–199, (1999); by A. J. Fatiadi in *Synthesis*, 85 (1987); and by P. Pietikainen, *J. Mol. Catal. A: Chem.*, 165, (1–2), pp. 73–79, (2001); all of which are incorporated herein by reference.

The use of recyclable, supported, heterogeneous manganese-based dihydroxylation catalysts is well-known to those skilled in the art and is described, for instance, by P. A. Jacobs, et al., in European Patent EP 970951; in *Angew. Chem. Int. Ed.*, 38, No. 7, pp. 980–983, (1999); and in *J. Molecular Catalysis A: Chemical*, 117, pp. 57–70, (1997); and by D. Brunel, et al., *Chem. Commun.*, pp. 2485–2486, (1996); all of which are incorporated herein by reference.

In yet another embodiment of the present invention, the transition metal catalysts useful as α-dihydroxylation catalysts are compounds or complexes of rhenium. The use of rhenium-based dihydroxylation catalysts is well-known to those skilled in the art and is comprehensively reviewed, for instance, by W. A. Hermann, et al., in *Chemical Reviews*, 97, (8), pp. 3197–3246, (1997) and in *Accounts of Chemical Research*, 30, (4), pp. 169–180, (1997); and by M. M. Abu-Omaret, et al., in *Catalysis Today*, 55, pp. 317–363, (2000); and is described, for instance, by W. A. Hermann, et al., *Angew. Chem., Int. Ed. Engl.*, 30, (12), pp. 1638–1643, (1991); by A. K. Rappe, et al., *Organometallics*, (17), pp. 2716–2719, (1998); by W. Adams, in *Angew. Chem., Int. Ed. Engl.*, 35, (5), pp. 533–535, (1996); and by J. Espenson, et al., in *J. Org. Chem.*, 61, pp. 3969–3976, (1996) and in *Inorg. Chem.*, Vol. 37, pp. 467–472, (1998); all of which are incorporated herein by reference.

In still another embodiment of the present invention, the transition metal compounds or complexes useful as α-dihydroxylation catalysts are compounds or complexes of ruthenium. The use of ruthenium-based dihydroxylation catalysts is well-known to those skilled in the art and is described, for instance, by T. K. M. Shing, et al., in *Angew. Chemie.*, 106, pp. 2408, (1994); in *Angew. Chemie Int. Ed.*

*Eng.,* 33, pp. 2312, (1994); in *Chem.-Eur. J.,* 2, pp. 50, (1996); and in *Tetrahedron Lett.,* 40, pp. 2179,(1999); all of which are incorporated herein by reference.

In an alternative, indirect dihydroxylation process, catalytic α-dihydroxylation of allyl ether groups of aryl allyl ether compounds, is done by oxidizing the allyl ether groups indirectly to the α-dihydroxy derivative. In the indirect dihydroxylation process, a transient epoxide group intermediate is formed first. The transient epoxide group intermediate may or may not be observed, and the transient epoxide groups of an aryl allyl ether compound are subsequently converted in situ in the presence of the dihydroxylation catalyst and oxidant material into the α-dihydroxy derivative. In the indirect α-dihydroxylation process, the reaction product is an α-dihydroxy derivative which may include small amounts of epoxide intermediate which were not transformed into the α-dihydroxy derivative. In the indirect α-dihydroxylation process, the conversion of the transient epoxy intermediate is caused by the acidic properties of the transition metal dihydroxylation catalyst.

In one embodiment of the present invention, the catalyst in an indirect α-dihydroxylation process may be a compound or complex of a transition metal or a Group VIA element selected from the group comprising, for example, W, Cr, Mo, Re, V, Ti, Se or mixtures thereof.

In yet another embodiment of the present invention, the transition metal compounds or complexes useful as indirect α-dihydroxylation catalysts are compounds or complexes of titanium. The use of titanium silicate molecular sieves as dihydroxylation catalysts under triphase reaction conditions is described by A. Bhaumik, et al., in *J. Catal.,* 176,(2), pp. 305–309, (1998); and by G. Thiele, et al., in U.S. Pat. No. 6,100,412; both of which are incorporated herein by reference.

The transition metal and Group VIB element complexes or compounds useful as α-dihydroxylation catalysts may be soluble and act as homogeneous catalysts or alternatively they may be covalently or ionically bound to a solid support and act as a heterogenous catalyst.

The transition metal and Group VIB element complexes or compounds useful as α-dihydroxylation catalysts may be racemic catalysts or they may be asymmetric catalysts, as taught in the known art.

The concentration of α-dihydroxylation catalyst useful in the present invention is preferably from about $1\times10^{-6}$ to about 1 mole of transition metal or Group VIB element catalyst per 1 mole of aryl allyl ether present in the reaction mixture.

When the dihydroxylation catalysts are heterogenous catalysts, the heterogeneous dihydroxylation catalysts are formulated so the total weight of the transition metal or Group VIB element relative to the weight of the solid support material is in the range of from about $1\times10^{-6}$ parts to about 1 part of transition metal or Group VIB element per 1 part of solid support. The amount of heterogeneous α-dihydroxylation catalyst useful in the present invention is preferably in the range of from about $10^3$ parts to about 100 parts of heterogeneous catalyst to 1 part of aryl allyl ether in the dihydroxylation reaction mixture.

The transition metal and Group VIB element complexes or compounds useful as α-dihydroxylation catalysts may be used in the presence of certain additives, co-catalysts, and co-oxidants.

Additives, Co-Catalysts, and Co-Oxidants for the Catalytic Dihydroxylation Process In one embodiment of the present invention, catalytic dihydroxylation of allyl ether groups of aryl allyl ether compounds is carried out by oxidizing the allyl ether groups in the presence of additives, co-catalysts, or co-oxidants.

The additives used in catalytic dihydroxylation of allyl ether groups of aryl allyl ether compounds include, for example, such compounds as tertiary amine compounds and compounds used to control dihydroxylation reaction pH between about 7.5 to about 13. Such compounds used to control reaction pH are described, for example, by M. Beller, et al., in PCT WO 2000064848 A1 and in *Tetrahedron Lett.,* 41, (42), pp. 8083–8087, (2000); both of which are incorporated herein by reference.

The co-catalysts used in catalytic dihydroxylation of allyl ether groups of aryl allyl ether compounds may include compounds which are hydrolysis aids such as, for example, salts of alkyl sulfonamides or alkyl carboxylates or methanesulfonamide which are described by K. Sharpless, et al., in *J. Org. Chem.,* 57, (10), pp. 2768–71, (1992), which is incorporated herein by reference.

The co-oxidants used in catalytic dihydroxylation of allyl ether groups of aryl allyl ether compounds include salts such as, for example, copper I and copper II salts, which are beneficial in reducing the energy requirement to re-oxidize the reduced form of the oxidant. Such co-oxidants are known to those skilled in the art. The co-oxidants are described for instance by J- E. Baeckvall, et al., in *J. Am. Chem. Soc.,* 121, (44), pp. 10424–10425, (1999); by K. Bergstad, et al., in *J. Am. Chem. Soc.,* 121, (44), pp. 10424–10425, (1999); A. E11, et al. *Tetrahedron Letters,* 42, 2569–2571, (2001); and by M. Mrksich, et al., *Langmuir,* 15, (15), pp. 4957–4959, (1999); all of which are incorporated herein by reference. Co-oxidants include, for example, naturally occurring flavones and their synthetic analogs, as well as several metal salts and complexes, such as for example, metal salts and complexes of V, Zr, Hf, Ti, Nb, Ta, W, Mo, Mn or mixtures thereof.

In one embodiment of the present invention, the amount of additive, co-catalyst, or co-oxidant used should not be detrimental to the α-dihydroxylation process. It is preferred to use an amount of additive, co-catalyst, or co-oxidant which is less than about $1\times10^{-3}$ mole to about 0.20 mole of the additive, co-catalyst, or co-oxidant per equivalent of aryl allyl ether moieties which are being reacted in the dihydroxylation process. More preferably the amount of additive, co-catalyst, or co-oxidant used is less than about $1\times10^{-3}$ mole to about 0.10 mole of the additive, co-catalyst, or co-oxidant per equivalent of aryl allyl ether moieties which are being reacted in the dihydroxylation process. Most preferably, the amount of additive, co-catalyst, or co-oxidant used may be less than about $1\times10^{-3}$ mole to about 0.05 mole of the additive, co-catalyst, or co-oxidant per equivalent of aryl allyl ether moieties which are being reacted in the dihydroxylation process.

Oxidants for the Catalytic Dihydroxylation Process

α-Dihydroxy derivatives, in general, and α-dihydroxy derivatives of aryl allyl ether, in particular, can be prepared by oxidizing the corresponding allyl ether by catalytic oxidation using, for example, air, oxygen, an oxygen-gas(es) mixture, hydrogen peroxide, terteriary organic amine N-oxides, organic hydroperoxides, periodate salts, hypochlorite salts, persulfate salts, or iron III salts as oxidants.

In one embodiment of the present invention, air or oxygen is preferably used as the oxidant for the dihyroxylation of aryl allyl ethers of the present invention. The use of air or oxygen as an oxidant for dihydroxylation is comprehensively reviewed by T. Wirth, *Angew. Chem., Int. Ed.,* 39, (2), pp. 334–335, (2000) and by R. G. Austin, et al., in *Catalysis* of *Organic Reactions,* R. L. Augustine, Editor, pp. 269 (1985); and described by R. C. Michaelson, et al., in U.S. Pat. Nos. 4,413,151 and 4,314,088; and in European Patent 0,077,201 A2; 19830628; by R. G. Austin, et al, in *Catalysis of Organic Reactions,* R. L. Augustine, Ed. pp. 269, (1985); by R. S. Meyers, et al., in U.S. Pat. No. 4,496,779; by R. C. Michaelson, et al., EP 0077201 A2 830420; by T. Wirth in *Angew. Chemie Int. Ed. Eng.,* 2, pp. 334, (2000); by C. Dobler, et al., in *Angew. Chemie Int. Ed. Eng.,* 38, pp. 3026, (1999); and by M. Beller, et al., in WO Patent Application 2000064844 A1 and in *J. Am. Chem. Soc.,* 122, (42), pp. 10289–10297, (2000); all of which are incorporated herein by reference.

When oxygen is used as oxidant in the catalytic dihydroxylation process, oxygen may be present as pure oxygen, or the oxygen may be present as a mixture of gases. It is preferred to use nitrogen in mixtures of gases containing oxygen. When oxygen is used as a mixture of gases, the oxygen is preferably present from about 1% to about 100% on a volume basis.

In another embodiment of the present invention, an oxidant useful in the dihyroxylation process for reacting aryl allyl ethers of the present invention is hydrogen peroxide as described by K. Bergstad, et al., *J. Am. Chem. Soc.,* 121, (44), pp. 10424–10425, (1999); and by A. E11, et al. *Tetrahedron Letters,* 42, 2569–2571, (2001); both of which are incorporated herein by reference. Generally, the hydrogen peroxide used is an aqueous hydrogen peroxide containing from about 3 to about 80 percent hydrogen peroxide by weight.

In yet another embodiment of the present invention, useful oxidants in the dihyroxylation process for reacting aryl allyl ethers of the present invention are tertiary organic amine N-oxides. Generally, the organic amine N-oxides used as the oxidizing agent in the α-dihydroxylation process of the present invention may be any organic compounds having at least one N-oxide ($\equiv$N—O) functional group. The amine N-oxides useful in the present invention preferably have the following general structure:

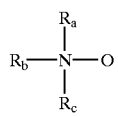

wherein $R_a$, $R_b$, and $R_c$ are the same or different; and $R_a$, $R_b$, and $R_c$ have from 1 to 12 carbon atoms; and $R_a$, $R_b$, and $R_c$ are selected from the group comprising an alkyl group, such as methyl or ethyl; a cycloaliphatic group, such as cyclohexyl; an aromatic group such as phenyl or benzyl; or any combination thereof. A combination of two or more of $R_a$, $R_b$, and $R_c$ can also be in the same structural unit such as in the case of a pinanyl group.

Organic amine N-oxides useful in the present invention include, for example, but are not limited to, trimethylamine N-oxide, triethylamine N-oxide, N-methyl morpholine N-oxide, and pyridine N-oxide. Mixtures of organic tertiary amine N-oxides may also be employed in the present invention.

The organic tertiary amine N-oxide may be pre-formed prior to its use by, for example, air-oxidation of a corresponding tertiary amine. Alternatively, the organic tertiary amine N-oxides may be formed in situ. The in situ process for making organic tertiary amine N-oxides is feasible, but is generally more difficult to control than pre-forming the organic tertiary amine N-oxides.

In still another embodiment of the present invention, useful oxidants in the dihyroxylation process for reacting aryl allyl ethers of the present invention are the organic hydroperoxides. Organic hydroperoxides used as the oxidizing agent in the α-dihydroxylaiton process of the present invention may be any organic compounds having at least one hydroperoxy (—OOH) functional group. However, tertiary hydroperoxides are preferred due to the higher instability and greater safety hazards associated with primary and secondary hydroperoxides. The organic hydroperoxide useful in the present invention preferably has the following general structure:

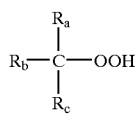

wherein $R_a$, $R_b$, and $R_c$ are the same or different; $R_a$, $R_b$, and $R_c$ have from 1 to 12 carbon atoms; and $R_a$, $R_b$, and $R_c$ are selected from the group comprising hydrogen; an alkyl group, such as methyl or ethyl; a cycloaliphatic group, such as cyclohexyl; an aromatic group such as phenyl or benzyl; or any combination thereof. A combination of two or more of $R_a$, $R_b$, and $R_c$ can also be in the same structural unit such as in the case of a pinanyl group.

Examples of organic hydroperoxides useful in the present invention include tert-butyl hydroperoxide; tert-amyl hydroperoxide; cumene hydroperoxide; ethyl benzene hydroperoxide; cyclohexane hydroperoxide; methyl cyclohexane hydroperoxide; pinane hydroperoxide; tetrahydronaphthalene hydroperoxide; isobutyl benzene hydroperoxide; isopropyl hydroperoxide; and ethyl naphthalene hydroperoxide. It is preferred that the hydroperoxide used is tert-butyl hydroperoxide or tert-amyl hydroperoxide. Mixtures of organic hydroperoxides may also be employed in the present invention.

The organic hydroperoxide may be pre-formed prior to its use by, for example, air-oxidation of a corresponding alkane or aromatic hydrocarbon. Alternatively, the organic hydroperoxide may be formed in situ. The in situ process for making organic hydroperoxide is feasible, but is generally more difficult to control than pre-forming the organic hydroperoxide.

In a preferred embodiment, the ratio of the oxidant used for dihydroxylation of the aryl allyl ether is preferably in the range of from about 0.6 mole to about 20 moles of oxidant to 1 equivalent of aryl allyl ether moiety. More preferably, the ratio of oxidant used for dihydroxylation to the aryl allyl ether is in the range of from about 1 mole to about 5 moles of oxidant to 1 equivalent of aryl allyl ether moiety. The most preferred ratio for oxidant used for dihydroxylation of the aryl allyl ether is from about 1 mole to about 2.5 moles of oxidant to 1 equivalent of aryl allyl ether moiety. One equivalent of oxidant is theoretically required to oxidize one equivalent of an aryl mono-allyl ether substrate, but it may be desirable to employ an excess of oxidant to optimize conversion to the α-dihydroxy derivative.

Process Conditions for Catalytic Dihydroxylation Process

The oxidation step to convert aryl allyl ethers to α-dihydroxy derivatives of the present invention may be carried out in a variety of ways known to those skilled in the art and, as outlined generally, for example, in the following publications: M. Beller, et al., *Appl. Homogeous Catal. Organomet. Compd.,* 2, B. Cornils and W. A. Herrmann, Eds. pp. 1009, (1996); H. C. Kolb, et al., *Chem. Rev.,* 94, pp. 2483, (1994); I. Marko, et al., *Comprehensive Asymmetric Catal. I–III,* E. N. Jacobsen, A. Pfaltz, and H. Yamamoto, Eds., pp. 713, (1999); and V. VanRheenen, et al., *Org. Syn.,*

*Coll. Vol. VI*, pp. 342, (1988); all of which are incorporated herein by reference.

To carry out the catalytic α-dihydroxylaiton process of the present invention using hydrogen peroxide oxidant, a tertiary amine N-oxide oxidant, or organic hydroperoxide oxidant, the oxidant hydrogen peroxide, amine N-oxide, or organic hydroperoxide may be added to a reactor in one batch together with one or more aryl allyl ethers represented by having Formula I to V. It is preferred to add the hydrogen peroxide, amine N-oxide, or organic hydroperoxide oxidant incrementally to the reactor when a large amount of hydrogen peroxide, amine N-oxide oxidant, or organic hydroperoxide oxidant is used.

In another embodiment, the oxidant such as, for example, hydrogen peroxide, the tertiary amine N-oxide, or organic hydroperoxide can be added concurrently with an aryl allyl ether into a reactor in a continuous fashion.

The temperature of the dihydroxylation process of the present invention should be sufficient to accomplish substantial conversion of the aryl allyl ether to the α-dihydroxy derivative within a reasonably short period of time. It is generally advantageous to carry out the α-dihydroxylation process to achieve as high conversion as possible, preferably at least greater than about 50 percent (%), more preferably at least greater than about 75%, and most preferably at least greater than about 90%, consistent with reasonable selectivities to the α-dihydroxy derivative. The optimum dihydroxylation process temperature will be influenced by catalyst activity, aryl allyl ether reactivity, reactant concentrations, and type of solvent employed, among other factors. But typically, the dihydroxylation process of the present invention is carried out at a temperature of from about −20° C. to about 150° C., preferably from about −15° C. to about 100° C., and more preferably from about −10° C. to about 80° C.

Preferably, in a dihydroxylation process, reaction times that vary from about 10 minutes to about 48 hours will typically be appropriate, depending upon the above-identified dihydroxylation reaction variables. More preferably, in a α-dihydroxylation process, the reaction time may vary from about 10 minutes to about 24 hours; and most preferably, in a α-dihydroxylation process, the reaction time may vary from about 10 minutes to about 2 hours.

The dihydroxylation process pressure may be atmospheric; sub-atmospheric, for example, from less than about 760 millimeters of mercury to about 5 millimeters of mercury; or super-atmospheric, for example, from about 1 atmosphere to about 100 atmospheres. Generally, it will be desirable to maintain the α-dihydroxylation process components as a liquid phase mixture.

The dihydroxylation process of the present invention may be carried out in a stirred batch, semi-continuous, or continuous manner using any appropriate type of process vessel or apparatus, provided the reaction mixture is adequately agitated. Thus, the reactants may be combined all at once or sequentially.

After the dihydroxylation process is completed, the α-dihydroxylation process mixture is subjected to separation and purification by known process operations and the excess, unused, organic oxidant, as well as, catalyst, additives, co-catalyst, and co-oxidants may be recovered and recycled, or destroyed and disposed of. For example, once the α-dihydroxylation process reaction has been completed to the desired amount of conversion, the desired α-dihydroxy derivative product may be separated and recovered from the dihydroxylation process mixture using appropriate techniques such as filtration, fractional distillation, extractive distillation, liquid—liquid extraction, solid-liquid extraction, crystallization, or any combination thereof.

In one embodiment of the present invention, the excess oxidant remaining after the dihydroxylation process may be recovered and recycled to the dihydroxylation process or the excess oxidant remaining after the dihydroxylation process may be decomposed by addition of a reducing agent.

The decomposition by-product of an α-dihydroxylation process using an organic hydroperoxide oxidant is a secondary or tertiary alcohol compound of the corresponding organic hydroperoxide oxidant. After isolation from the dihydroxylation reaction mixture, the alcohol decomposition product of the organic hydroperoxide can be dehydrated and hydrogenate or reacted directly under hydrogenolysis conditions to the corresponding alkane or aromatic hydrocarbon of the organic hydroperoxide oxidant. The alkane or aromatic hydrocarbon product may be reoxidized to the hydroperoxide and recycled to the α-dihydroxylation oxidation process.

Solvents

The dihydroxylation process of the present invention may be carried out optionally in the presence of a solvent. Solvents that may be used in the dihydroxylation process mixture of the present invention include solvents that do not react with the inorganic or organic oxidant, catalyst, additive, co-catalyst, or co-oxidant used in the dihydroxylation process mixture of the present invention, but in which they are at least partially soluble. For example, some solvents, such as dimethylsulfoxide, will react with an organic hydroperoxide, such as tert-butyl hydroperoxide. Solvents which can be used in the present invention include, for example, aliphatic, cycloaliphatic or aromatic hydrocarbon solvents; partially or fully chlorinated or fluorinated, or combinations thereof; aliphatic, cycloaliphatic or aromatic esters, ethers, alcohols, ketones and nitrites; and partially or fully chlorinated or fluorinated aliphatic, cycloaliphatic or aromatic ester, ether, alcohol, ketones, and nitrile solvents; water; and combinations thereof.

Solvents especially useful in the dihydroxylation process include alcohols such as tertiary butyl alcohol, ketones such as acetone, other non-reactive, water-miscible solvents, and mixtures thereof.

In another embodiment of the present invention, solvents which may be used in the present invention are solvents that may be used under dense phase or supercritical conditions. Such solvents include, for example, but are not limited to, carbon dioxide, ethane, dimethyl ether, and mixtures thereof.

The solvent useful in the present invention is generally employed in an amount of from 0 parts by weight to about 100 parts by weight of solvent per one part of substrate reactant aryl allyl ether. Preferably, the amount of solvent used is from 0 parts to about 25 parts by weight of solvent per one part of substrate reactant aryl allyl ether; and more preferably, the amount of solvent used is from 0 parts to about 10 parts by weight of solvent per one part of substrate reactant aryl allyl ether.

The α-dihydroxy derivatives of the present invention prepared above can be converted into epoxy compounds by various means well-known to those skilled in the art.

Epoxy Compounds

The aryl glycidyl ether epoxy compounds that are made by the process of the present invention are represented by, but not limited to, the structures of the following Formulas XVI–XX:

Formula XVI

In Formula XVI, x, y, Ar, O and $R^1$ are as defined previously for Formula I.

In Formula XVI, $R^5$ is a glycidyl-containing moiety preferably selected from:

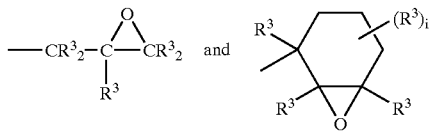

where $R^3$ and i are as defined previously for Formula I.

In one embodiment, when $R^5$ in Formula XVI above has the following structure:

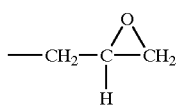

the glycidyl ether is a "glycidyl ether."

In another embodiment, when $R^5$ in Formula XVI above has the following structure:

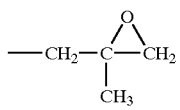

the glycidyl ether is a "methylglycidyl ether."

In yet another embodiment, when $R^5$ in Formula XVI above has the following structure:

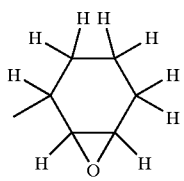

the glycidyl ether is a "cyclohexylglycidyl ether."

More specific and preferred examples of epoxy resins that may be prepared according to the present invention are represented by Formulas XVII–XX separately or mixtures of two or more epoxy resins which follow.

Examples of mononuclear aryl glycidyl ether epoxy resins that may be prepared according to the present invention are represented by the following Formula XVII:

Formula XVII

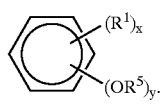

In Formula XVII, x, y, O and $R^1$ have the same meaning as described above with reference to Formula II. In Formula XVII, $R^5$ has the same meaning as described above with reference to Formula XVI.

Mononuclear phenols useful as precursors for preparing the above mononuclear aryl glycidyl ether epoxy resins of the present invention are, for example, 2-methylphenol; 4-methylphenol; 4-methoxyphenol; 2,6-dimethylphenol; 2,6-diisopropylphenol; 2,6-dibromophenol; 1,2-, 1,3- and 1,4-dihydroxybenzene; 1,4-, 1,5- and 2,6-dihydroxynaphthalene; and mixtures thereof.

Other examples of aryl glycidyl ethers prepared by the process of the present invention are dinuclear aryl glycidyl ether epoxy resins that are represented by the following Formula XVIII:

Formula XVIII

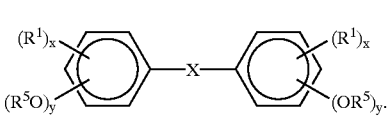

In Formula XVIII, x, y, X, O and $R^1$ have the same meaning as described above with reference to Formula III. In Formula XVIII, $R^5$ has the same meaning as described above with reference to Formula XVI.

Phenols useful for making the epoxy resins of Formula XVIII include, for example, 4,4'-dihydroxybiphenyl; 3,3',5, 5'-tetramethyl-4,4'-dihydroxybiphenyl; 3,3',5,5'-tetramethyl-2,2',6,6'-tetrabromo-4,4'-dihydroxybiphenyl; bis(4-hydroxyphenyl)methane; bis(4-hydroxyphenyl) sulfone; 2,2-bis(3,5-dibromo-4-hydroxyphenyl) isopropylidene; 2,2-bis(4-hydroxyphenyl)isopropylidene; bisphenol K; 9,9-bis(4-hydroxyphenyl)fluorene; 4,4'-dihydroxy-α-methylstilbene; 1,3-bis(4-hydroxylphenyl) adamantane; and mixtures thereof.

Other examples of aryl glycidyl ethers prepared by the process of the present invention are multi-nuclear aryl glycidyl ether epoxy resins that are represented by the following Formula XIX:

Formula XIX

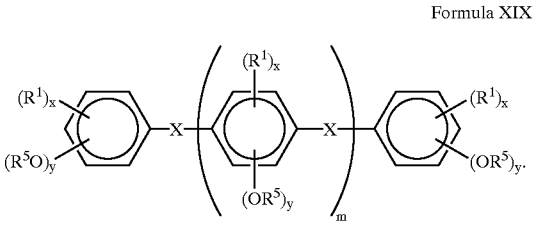

In Formula XIX, x, y, X, O, $R^1$ and m are as described above for Formula IV. In Formula XIX, $R^5$ has the same meaning as described above with reference to Formula XVI.

Phenols useful for making the epoxy resins of Formula XIX include, for example, phenol-formaldehyde novolac (functionality greater than 2); o-cresol-formaldehyde novolac (functionality greater than 2); phenol-dicyclopentadienyl novolac (functionality greater than 2); naphthol-formaldehyde novolac (functionality greater than 2); and mixtures thereof.

Still other examples of aryl glycidyl ethers prepared by the process of the present invention are multi-nuclear aryl glycidyl ether epoxy resins that are represented by the following Formula XX:

Formula XX

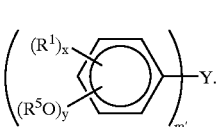

In Formula XX, x, y, Y, O, $R^1$ and m' are the same as previously described above for Formula V. In Formula XXI, $R^5$ has the same meaning as described previously with reference to Formula XVI.

Phenols useful for making the epoxy resins of Formula XX include, for example, tris(4-hydroxyphenyl) methane; tris(3,5-dimethyl-4-hydroxyphenyl)methane; 1,1,2,2-tetrakis(4-hydroxyphenyl)ethane; and mixtures thereof.

Examples of preferred aryl glycidyl ether epoxy resins of the present invention include, for example, 2-methylphenol glycidyl ether; 4-methylphenol glycidyl ether; 4-methoxyphenol glycidyl ether; 2,6-dimethylphenol glycidyl ether; 2,6-diisopropylphenol glycidyl ether; 2,6-dibromophenol glycidyl ether; 1,2-, 1,3- and 1,4-dihydroxybenzene diglycidyl ethers; 1,4-, 1,5- and 2,6-dihydroxynaphthalene diglycidyl ethers; 4,4'-(3,3',5,5'-tetramethyl)bisphenol A diglycidyl ether; 4,4'-(3,3',5,5'-tetramethyl-2,2',6,6'-tetrabromo)bisphenol A diglycidyl ether; 4,4'-(3,3',5,5'-tetramethyl)bisphenol F diglycidyl ether; 4,4'-(3,3'5,5'-tetramethyl)biphenol diglycidyl ether; 4,4'-biphenol diglycidyl ether; 4,4'-(3,3'5,5'-tetramethyl-2,2',6,6'-tetrabromo)biphenol diglycidyl ether; 4,4'-bisphenol F diglycidyl ether; 4,4'-bisphenol sulfone diglycidyl ether; 4,4'-(3,3',5,5'-tetrabromo)bisphenol A diglycidyl ether; 4,4'-bisphenol A diglycidyl ether; 4,4'-bisphenol K diglycidyl ether; 9,9-bis(4-hydroxyphenyl)fluorene diglycidyl ether; 4,4'-dihydroxy-α-methylstilbene diglycidyl ether; 1,3-bis(4-hydroxyphenyl)adamantane diglycidyl ether; phenol-formaldehyde novolac glycidyl ether (functionality>2); o-cresol-formaldehyde novolac glycidyl ether (functionality>2); phenol-dicyclopentadienyl novolac glycidyl ether (functionality>2); naphthol-formaldehyde novolac glycidyl ether (functionality>2); trisphenylol methane triglycidyl ether; tris(3,5-dimethyl-4-hydroxyphenyl) methane triglycidyl ether; 1,1,2,2-tetraphenylol ethane tetraglycidyl ether; and mixtures thereof.

The epoxy resins described above may be prepared by various processes utilizing the α-dihydroxy derivatives of the present invention including for example via an intermediate such as (1) a carbonate such as described in U.S. Pat. No. 6,005,063 and in WO 99/09020, both of which are incorporated herein by reference, or (2) an α-halohydrin intermediate such as described in U.S. Pat. No. 6,001,945, incorporated herein by reference. The epoxy resin of the present invention is preferably produced by first forming an α-halohydrin intermediate from an allyl ether, and then converting the α-halohydrin intermediate into the epoxy compound.

α-Halohydrin Intermediates

The present invention includes a process for manufacturing an α-halohydrin intermediate from an α-dihydroxy derivative. The α-halohydrin intermediate is then used to make epoxy resins.

Generally, the process of the present invention for manufacturing the α-halohydrin intermediate includes converting an α-dihydroxy derivative to the α-halohydrin intermediate by a halide substitution process using a hydrogen halide and a catalytic amount of a carboxylic acid or carboxylic acid ester; or by a halide substitution process using a hydrogen halide and a carboxylic acid ester as solvent. Then, the α-halohydrin intermediate can be used to make epoxy resins by well-known techniques in the industry, such as, for example, by a ring-closing epoxidation reaction of the α-halohydrin intermediate with a base. More preferably, the epoxy resins which can be prepared by the process of the present invention include, for example, bisphenol A (bis A) diglycidyl ether epoxy resin also known as BADGE.

The α-halohydrin intermediates prepared in accordance with the process of the present invention are represented for example by, but not limited to, the structures of the following Formulas XXI–XXV. A preferred class of α-halohydrin intermediates useful in the present invention is generically represented for example by the following Formula XXI:

Formula XXI

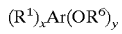

In Formula XXI, x, y, Ar, O, and $R^1$ are as defined in Formula I.

In Formula XXI, $R^6$ is an α-halohydrin propyl-containing moiety preferably selected from:

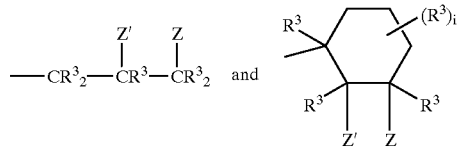

where Z is a halogen atom such as chlorine, bromine or iodine; and Z' is a hydroxyl group. The positions of Z and Z' may be interchanged. $R^3$ and i in Formula XXI are as previously defined in Formula I.

In one embodiment, when $R^6$ in Formula, I above is the following structure:

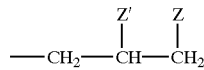

the α-halohydrin is a 3-halo-2-hydroxy-1-propyl moiety-containing derivative; or in such derivative, the hydroxy and halo groups may be interchanged to form a 2-halo-3-hydroxy-1-propyl moiety-containing derivative.

In another embodiment, when $R^6$ in Formula XXI above is the following structure:

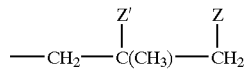

the α-halohydrin is a 3-halo-2-hydroxy-2-methyl-1-propyl moiety-containing derivative; or in such derivative, the hydroxy and halo groups may be interchanged to form a 2-halo-3-hydroxy-2-methyl-1-propyl moiety-containing derivative.

In yet another embodiment, when $R^6$ in Formula XXI above is the following structure:

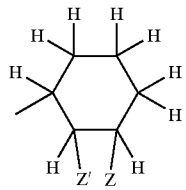

the α-halohydrin is a 3-halo-2-hydroxy-1-cyclohexyl moiety-containing derivative; or in such derivative, the hydroxy and halo groups may be interchanged to form a 2-halo-3-hydroxy-1-cyclohexyl moiety-containing derivative. In both derivatives, the propyl moiety is contained in the cyclohexyl ring structure.

More specific and preferred examples of α-halohydrin intermediates useful in the present invention are represented by Formulas XXII–XXV separately or as mixtures of two or more α-halohydrin intermediates of Formulas XXII–XXV which follow.

Examples of mononuclear aromatic α-halohydrin intermediates useful in the present invention are represented for example by the following Formula XXII:

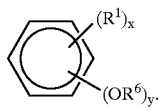

Formula XXII

In Formula XXII, x, y, O, and $R^1$ have the same meaning as described above with reference to Formula II. In Formula XXII, $R^6$ has the same meaning as described above with reference to Formula XXI. α-Halohydrin intermediates of Formula XXII can be prepared from phenolic compounds or aromatic hydroxyl group-containing precursors, such as, for example, 2-methylphenol; 4-methylphenol; 4-methoxyphenol; 2,6-dimethylphenol; 2,6-diisopropylphenol; 2,6-dibromophenol; 1,2-dihydroxybenzene; 1,3-dihyroxybenzene; 1,4-dihydroxybenzene; 1,4-, 1,5- and 2,6-dihydroxynaphthalene; and mixtures thereof.

Other examples of α-halohydrin intermediates useful in the present invention are binuclear aromatic α-halohydrin intermediates which are represented, for example, by the following Formula XXIII:

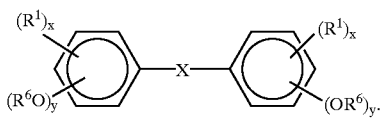

Formula XXIII

In Formula XXIII, x, y, X, O and $R^1$ have the same meaning as described above with reference to Formula III. In Formula XXIII, $R^6$ has the same meaning as described above with reference to Formula XXI.

Precursors useful for making the α-halohydrin intermediates of Formula XXIII include, for example, 4,4'-dihydroxybiphenyl; 3,3',5,5'-tetramethyl-4,4'-dihydroxybiphenyl; 3,3',5,5'-tetramethyl-2,2',6,6'-tetrabromo-4,4'-dihydroxybiphenyl; bis(4-hydroxyphenyl)methane; bis(4-hydroxyphenyl)sulfone; 2,2-bis(3,5-dibromo-4-hydroxyphenyl)isopropylidene; 2,2-bis(4-hydroxyphenyl)isopropylidene; bisphenol K; 9,9-bis(4-hydroxyphenyl)fluorene; 4,4'-dihydroxy-α-methylstilbene; 1,3-bis(4-hydroxylphenyl)adamantane; and mixtures thereof.

Other examples of α-halohydrin intermediates useful in the present invention are multinuclear aromatic α-halohydrin intermediates which are represented, for example, by the following Formula XXIV:

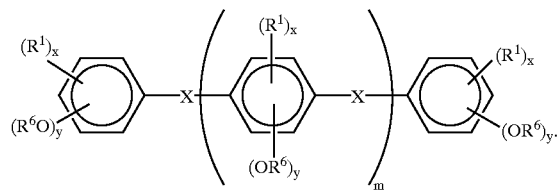

Formula XXIV

In Formula XXIV, x, y, O, X, $R_1$ and m have the same meaning as has been previously described above in Formula III. In Formula XXIV, $R^6$ has the same meaning as described above with reference to Formula XXI.

Precursors useful for making the α-halohydrin intermediates of Formula XXIV include, for example, phenol-formaldehyde novolac (functionality greater than 2); o-cresol-formaldehyde novolac (functionality greater than 2); phenol-dicyclopentadienyl novolac (functionality greater than 2); naphthol-formaldehyde novolac (functionality greater than 2); and mixtures thereof.

Other examples of α-halohydrin intermediates useful in the present invention are multi-nuclear aromatic α-halohydrin intermediates which are represented, for example, by the following Formula XXV:

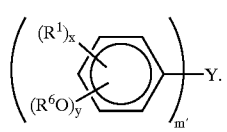

Formla XXV

In Formula XXV, x, y, O, $R^1$, Y and m' have the same meaning as has been previously described above in Formula V. In Formula XXV, $R^6$ has the same meaning as described previously with reference to Formula XXI.

Precursors useful for making the α-halohydrin intermediates of Formula XXV include, for example, tris(4-hydroxyphenyl)methane; 1,1,1-tris(3,5-dimethyl-4-hydroxyphenyl)methane; 1,1,2,2-tetrakis(4-hydroxyphenyl)ethane; and mixtures thereof.

Preferably, the α-halohydrin intermediates of the present invention, include for example(3-chloro-2-hydroxy-1-propyl) ether of 2-methylphenol; (3-chloro-2-hydroxy-1-propyl) ether of 4-methylphenol; (3-chloro-2-hydroxy-1-propyl) ether of 4-methoxyphenol; (3-chloro-2-hydroxy-1-propyl) ether of 2,6-dimethylphenol; (3-chloro-2-hydroxy-1-propyl) ether of 2,6-diisopropylphenol; (3-chloro-2-hydroxy-1-propyl) ether of 2,6-dibromophenol; bis(3-chloro-2-hydroxy-1-propyl) ether of 1,2-, 1,3- and 1,4-dihydroxybenzene; bis(3-chloro-2-hydroxy-1-propyl) ether of 1,4-, 1,5- and 2,6-dihydroxynaphthalene; bis(3-chloro-2-hydroxy-1-propyl) ether of 4,4'-(3,3',5,5'-tetramethyl) bisphenol A; bis(3-chloro-2-hydroxy-1-propyl) ether of 4,4'-(3,3',5,5'-tetramethyl-2,2',6,6'-tetrabromo)bisphenol A; bis (3-chloro-2-hydroxy-1-propyl)ether of 4,4'-(3,3',5,5'-tetramethyl)bisphenol F; bis(3-chloro-2-hydroxy-1-propyl) ether of 4,4'-(3,3'5,5'-tetramethyl)biphenol; bis(3-chloro-2-hydroxy-1-propyl) ether of 4,4'-biphenol; bis(3-chloro-2-hydroxy-1-propyl) ether of 4,4'-(3,3'5,5'-tetramethyl-2,2',6,6'-tetrabromo)biphenol; bis(3-chloro-2-hydroxy-1-propyl) ether of 4,4'-bisphenol F; bis(3-chloro-2-hydroxy-1-propyl) ether of 4,4'-bisphenol sulfone; bis(3-chloro-2-hydroxy-1-propyl) ether of 4,4'-(3,3',5,5'-tetrabromo)bisphenol A; bis (3-chloro-2-hydroxy-1-propyl) ether of 4,4'-bisphenol A; bis(3-chloro-2-hydroxy-1-propyl)ether of 4,4'-bisphenol K;

bis(3-chloro-2-hydroxy-1-propyl) ether of 9,9-bis(4-hydroxyphenyl)fluorene; bis(3-chloro-2-hydroxy-1-propyl) ether of 4,4'-dihydroxy-α-methylstilbene; bis(3-chloro-2-hydroxy-1-propyl) ether of 1,3-bis(4-hydroxyphenyl) adamantane; (3-chloro-2-hydroxy-1-propyl) ether of phenol-formaldehyde novolac (functionality>2); (3-chloro-2-hydroxy-1-propyl) ether of o-cresol-formaldehyde novolac (functionality>2); (3-chloro-2-hydroxy-1-propyl) ether of phenol-dicyclopentadienyl novolac (functionality>2); (3-chloro-2-hydroxy-1-propyl)ether of naphthol-formaldehyde novolac (functionality>2); tri(3-chloro-2-hydroxy-1-propyl) ether of trisphenylol methane; tri(3-chloro-2-hydroxy-1-propyl) ether of tris(3,5-dimethyl-4-hydroxyphenyl)methane; tetra-(3-chloro-2-hydroxy-1-propyl) ether of 1,1,2,2-tetraphenylol ethane; and mixtures thereof.

In addition, the chloro and hydroxyl groups in the above 3-chloro-2-hydroxyl-1-propyl moiety-containing derivatives may be interchanged to form 3-hydroxy-2-chloro-1-propyl moiety-containing derivatives.

The α-halohydrin intermediates of the present invention comprise from about 10 to about 100 percent, more preferably from about 25 to about 100 percent, most preferably from about 50 to about 100 percent, of the total weight of one, or more than one, component(s) as illustrated in the above Formulas XXI–XXV.

The α-halohydrin intermediates of the present invention, for example as illustrated in the above Formulas XXI–XXV, are prepared by first obtaining an α-dihydroxy derivative and then converting the α-dihydroxy derivative to the α-halohydrin intermediate using a halide substitution process. More particularly, the α-halohydrin intermediates of the present invention are prepared by reacting the following components: (A) an α-dihydroxy derivative, (B) a hydrogen halide, (C) a catalytic amount of (i) a carboxylic acid or (ii) a carboxylic acid ester, in the presence of (D) a carboxylic acid ester solvent, and optionally, in the presence of (E) a non-carboxylic acid ester solvent.

The hydrogen halide, Component (B), useful in manufacturing the α-halohydrin intermediates of the present invention may include, for example, hydrogen chloride, hydrogen bromide or hydrogen iodide.

The amount of hydrogen halide, Component (B), useful in manufacturing the α-halohydrin intermediates of the present invention should be sufficient to ensure substantially complete conversion of the α-dihydroxy derivative to the α-halohydrin intermediate. The amount of hydrogen halide used is generally from about 0.50 mole to about 20 moles of hydrogen halide relative to the equivalents of α-dihydroxy moieties being reacted in the α-dihydroxy derivative; preferably from about 0.75 mole to about 10 moles of hydrogen halide relative to the equivalents of α-dihydroxy moieties being reacted in the α-dihydroxy derivative; and more preferably from about 0.95 mole to about 5 moles of hydrogen halide relative to the equivalents of α-dihydroxy moieties being reacted in the α-dihydroxy derivative.

The hydrogen halide may be added neat to the reaction as a liquid or as a gas. When added to the reaction as a gas, the hydrogen halide may be added as a continuous stream of gas. The hydrogen halide may also be dissolved in a solvent, such as those described in reference to Component (E) below, and added to the reactor as a solution. When an amount of halogen halide in excess of the stoichiometric amount necessary to ensure complete conversion of the of α-dihydroxy derivative is used, the excess amount may be removed from the reaction mixture by washing with water or careful neutralization with a base. It is preferred to recover and recycle the excess hydrogen halide by distilling the hydrogen halide from the reaction mixture.

The carboxylic acid, Component (C), useful in manufacturing the α-halohydrin intermediate of the present invention is a carboxylic acid having from 1 to 20 carbon atoms. The carboxylic acid, Component (C), useful in manufacturing the α-halohydrin intermediate of the present invention may include, for example monocarboxylic acids, such as, acetic acid, propionic acid, propenoic acid, hexanoic acid, cyclohexanoic acid, benzoic acid; dicarboxylic acids, such as, 1,4-butanedioic acid, 1,6-hexanedioic acid, 1,2-cyclohexandioic acid; or multifunctional carboxylic acid wherein the carboxylic acid groups are attached to an inorganic, an organic, or a hybrid inorganic-organic support, such as a weak acid, crosslinked, ion exchange resin; and mixtures thereof.

The amount of carboxylic acid, Component (C), used as catalyst in the halide substitution process may vary from about 0.05 mole % to about 50 mole % of carboxylic acid relative to the moles of α-dihydroxy derivative being reacted; preferably, the amount of carboxylic acid used may vary from about 0.05 mole % to about 25 mole % of carboxylic acid relative to the moles of α-dihydroxy derivative being reacted; and most preferably, the amount of carboxylic acid used may vary from about 0.05 mole % to about 10 mole % of carboxylic acid relative to the moles of α-dihydroxy derivative being reacted.

The carboxylic acid ester, Component (C), useful in manufacturing the α-halohydrin intermediate of the present invention is an ester of a monocarboxylic acid or dicarboxylic acid having 1 to 20 carbon atoms. The monocarboxylic acid or dicarboxylic acid moiety of the carboxylic acid ester may contain, for example, one or more heteroatoms selected from the group comprising O, N, S, Si, B, P, Cl and F. The monocarboxylic acid or dicarboxylic acid of the carboxylic acid ester is selected, for example, from the group comprising acetic acid, propionic acid, propenoic acid, 2-methylpropenoic acid, butanoic acid, 1,4-butanedioic acid, hexanoic acid, 1,6-hexanedioic acid, cyclohexanoic acid, 1,2-cyclohexandioic acid, benzoic acid, and mixtures thereof.

The carboxylic acid ester, Component (C) and (D), useful in manufacturing the α-halohydrin intermediate of the present invention is, for example, the ester of an aliphatic mono alcohol, diol, or triol having 1 to 12 carbon atoms, and the hydroxyl group(s) of the aliphatic mono alcohol, diol, or triol is a primary or secondary hydroxyl group. The aliphatic mono alcohol, diol, or triol moeity of the carboxylic acid ester may contain, for example, one or more heteroatoms selected from the group comprising O, N, S, Si, B, P, Cl and F. The aliphatic mono alcohol, diol, or triol is selected, for example, from the group comprising methanol, ethanol, propanol, isopropanol, 1-butanol, 2-butanol, isobutanol, cyclohexanol, benzyl alcohol, 1-methoxy-2-propanol, 1-ethoxy-2-propanol, ethylene glycol, diethylene glycol, propylene glycol, diproplene glycol, glycerine, trimethylolpropane, and mixtures thereof.

The carboxylic acid ester, Component (C), useful in manufacturing the α-halohydrin intermediate of the present invention is selected, for example, from the group comprising ethyl acetate, propyl acetate, isopropyl acetate, 1-methoxy-2-propanol acetate, butyl acetate, ethylene glycol diacetate, propylene glycol diacetate, trimethylolpropane triacetate, and mixtures thereof.

The amount of carboxylic acid ester Component (C), used as catalyst in the halide substitution process to convert the α-dihydroxy derivative to the α-halohydrin intermediate may vary from about 0.05 mole % to about 50 mole % of carboxylic acid ester relative to the moles of α-dihydroxy derivative being reacted; preferably, the amount of carboxylic acid ester used may vary from about 0.05 mole % to about 25 mole % of carboxylic acid ester relative to the moles of α-dihydroxy derivative being reacted; and most preferably, the amount of carboxylic acid ester used may vary from about 0.05 mole % to about 10 mole % of carboxylic acid ester relative to the moles of α-dihydroxy derivative being reacted.

The amount of carboxylic acid ester, Component (D), used as a solvent in the halide substitution process to convert the α-dihydroxy derivative to the α-halohydrin intermediate is from about 0.01 to about 100 parts (on a weight basis) of carboxylic acid ester to 1 part α-dihydroxy derivative. More preferably, the amount of carboxylic acid ester, Component (D), used as a solvent in the halide substitution process to convert the α-dihydroxy derivative to the α-halohydrin intermediate is from about 0.01 to about 10 parts (on a weight basis) of carboxylic acid ester to 1 part α-dihydroxy derivative; and most preferably, the amount of carboxylic acid ester, Component (D), used as a solvent in the halide substitution process to convert the α-dihydroxy derivative to the α-halohydrin intermediate is from about 0.01 to about 5 parts (on a weight basis) of carboxylic acid ester to 1 part α-dihydroxy derivative The non-carboxylic acid ester solvent, optional Component (E), which may be used in the above process for making the α-halohydrin intermediate may be, but is not limited to, aliphatic and cyclic hydrocarbons such as pentane, hexane, octane, iso-octane, cyclohexane and cyclooctane; aromatic hydrocarbons such as benzene, toluene and xylene; chlorinated solvents such as, for example, methylene dichloride, tetrachloroethane and chlorobenzene; aprotic solvents such as acetone, methyl iso-butyl ketone, acetonitrile, dimethoxyethane, 2,2'-dimethoxy diethyl ether, dioxane, dimethyl sulfoxide and 1-methoxy-2-acetoxypropane; protic solvents such as, for example, ethanol, 1-propanol, isopropyl alcohol, 1-butanol, 2-butanol, tert-butanol, 1-pentanol, tert-amyl alcohol, 1-hexanol, cyclohexanol and 1-methoxy-2-hydroxypropane; partially or fully fluorinated derivatives thereof; and any combination thereof. Optionally, the solvent may be used with or without the presence of water.

When protic alcohol solvents are optionally used, it is preferred that the alcohol solvents are secondary or tertiary alcoholic solvents, such as isopropyl alcohol, 2-butanol, tert-butanol, tert-amyl alcohol and 1-methoxy-2-hydroxypropane; partially or fully fluorinated derivatives thereof; and any combination thereof.

In general, the amount of the non-carboxylic acid ester solvent, optional Component (E), used in the present invention may be a ratio of from 0 to about 50 parts (on a weight basis) of a single solvent or a mixture of two or more solvents to 1 part α-dihydroxy derivative. A more preferred solvent to α-dihydroxy derivative ratio is from 0 to about 10 parts solvent per 1 part α-dihydroxy derivative. The most preferred solvent to α-dihydroxy derivative ratio is from 0 to about 5 parts solvent per 1 part α-dihydroxy derivative.

The temperature in the above reaction process for halide substitution of the α-dihydroxy derivative is generally from about 0° C. to about 150° C.; preferably from about 20° C. to about 130° C.; and more preferably from about 40° C. to about 110° C. At a temperature below 0° C., the reaction is not complete. At a temperature above about 150° C., undesirable chlorination reactions may take place.

The pressure used in the above reaction process for halide substitution of the α-dihydroxy derivative for manufacturing the α-chlorohydrin intermediate may be atmospheric, subatmospheric or superatmospheric. The pressure is not critical and may be determined by parameters such as type of hydrogen halide used, reaction temperature, type of solvent used or the solvent azeotrope boiling point.

The halide substitution of α-dihydroxy derivative to make the α-halohydrin intermediate can be carried out in a batch or in a continuous reaction mode. In a batch reaction, the α-dihydroxy derivative is optionally dissolved in a solvent, and the carboxylic acid, or the carboxylic acid ester, and the hydrogen halide are added to the reactor. In a batch process, it is highly desirable to run the reaction under pressure to maintain the hydrogen halide in the solution phase. When the batch reaction using hydrogen halide in solution phase is completed, the excess hydrogen halide and the carboxylic acid, or the carboxylic acid ester, may be removed from the reaction mixture by washing with water, by careful neutralization with a base, or by distillation. Or, the excess hydrogen halide and the carboxylic acid or the carboxylic acid ester may be recovered and recycled as described below.

In some instances, for example when using hydrogen chloride gas, it may be beneficial to purge the gas continuously through a reactor while efficiently mixing or agitating the reaction mixture in the reactor. In this process, the hydrogen chloride gas exiting the reactor is collected and recycled to the reactor.

In a continuous halide substitution process, the α-dihydroxy derivative and the carboxylic acid or carboxylic acid ester can optionally be mixed with a solvent and then intimately mixed with hydrogen halide as the carboxylic acid or carboxylic acid ester and α-dihydroxy derivative and optionally solvent is fed into a reactor. The reactors which may be used are well known in the art, for example, the reactor may be of a tubular design. After the reaction product leaves the reactor, the reaction product may pass through a series of purification steps. For example, in one embodiment when a solvent and a carboxylic acid are used and the solvent used boils at a lower temperature than the carboxylic acid, the reaction product may be: first, distilled to remove excess hydrogen halide where the hydrogen halide may then be recycled to the halide substitution reactor; second, distilled to remove the solvent, wherein the solvent may then be recycled to a halide substitution unit; and third, distilled to remove the carboxylic acid wherein the carboxylic acid product may then be recycled to the halide substitution unit.

In another second embodiment, when a solvent and a carboxylic acid are used, and the solvent used boils at a higher temperature than the carboxylic acid, the reaction product may be: first, distilled to remove the hydrogen halide wherein the hydrogen halide may then be recycled to the halide substitution reactor; and second, distilled to remove the carboxylic acid. In the second embodiment above, the solvent may optionally be removed for example by distillation, or the solvent need not be removed, wherein the solvent is carried forward as a solvent for a subsequent epoxidation step. The distillation steps described above may be carried out at atmospheric pressure, under subatmospheric pressure or under superatmospheric pressure as is well known in the art.

It is highly desirable and preferred to carry out the above processes whereby the α-halohydrin intermediate can be converted to the epoxy resin without additional purification.

The halide substitution of the α-dihydroxy derivative to make the α-halohydrin intermediate of the present invention is illustrated by the following reaction sequence, Reaction Sequence (IV), which shows the chloride substitution of an α-dihydroxy derivative. More specifically, Reaction Sequence (IV) shows the chloride substitution of an α-dihydroxy derivative to synthesize an α-chlorohydrin intermediate of the present invention.

Reaction Sequence (IV)

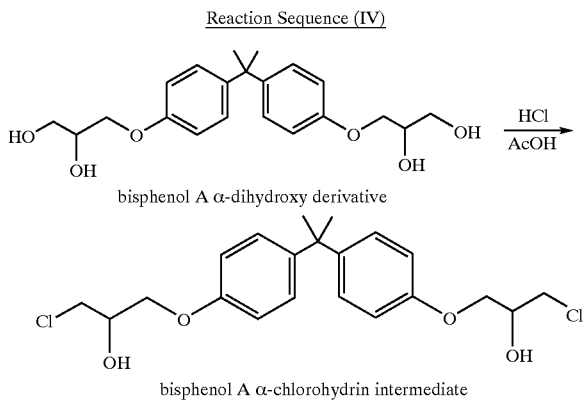

bisphenol A α-dihydroxy derivative bisphenol A α-chlorohydrin intermediate

The α-halohydrin intermediate of the present invention described above, can be converted to the epoxy resin by standard procedures well known to those skilled in the art using bases such as sodium hydroxide, calcium hydroxide, potassium hydroxide, sodium carbonate or mixtures thereof. The epoxidation procedures may be run with a solvent or mixture of solvents, or without solvent. The epoxidation procedures are typically run at elevated temperatures which may vary from about 10° C. to about 130° C. The epoxidation procedures may be run under atomospheric or under subatomospheric pressure.

The epoxidation procedures may also be run under conditions that do not remove the water which is introduced with the base and which forms in the reaction, or the epoxidation procedures may be run under conditions that remove the water under azeotropic conditions. It is desired to run the epoxidation procedures under conditions that remove water by azeotropic distillation in order to produce epoxy resins having higher epoxide content. The epoxidation procedures may be run including phase transfer catalysts, for example, such as the same phase transfer catalysts described previously.

The epoxidation procedures may be carried out as a batch reaction wherein the base may be added in one part initially, added intermittently or added continuously. The epoxidation procedure may also be carried out as a continuous reaction wherein the α-halohydrin intermediate, the base, the solvent and optionally the phase transfer catalyst are added simultaneously and continuously to a reactor. When the epoxidation procedure is carried out as a continuous reaction, the reactor may be a single, one-stage reactor or the reactor may be a complex reactor having multiple stages. Such epoxidation procedures, including post-treatment procedures for reducing chloride content in epoxy resins, are generally taught in U.S. Pat. Nos. 4,499,255; 4,778,863; 4,785,061; and 5,028,686; all of which are incorporated herein by reference.

With reference back to the α-dihydroxy derivative, Component (A) above, the α-dihydroxy derivative is preferably prepared by reaction of a phenolic compound or a mixture of phenolic compounds with an allylation agent.

When the α-dihydroxy derivative, Component (A), is prepared by the above process and such process is combined with the above-described process for preparing an α-halohydrin intermediate from the α-dihydroxy derivative and with a process for making an epoxy resin from the α-halohydrin, generally, the process of the present invention for making phenol-based epoxy resins may be illustrated by the following four-step process which is one embodiment of the present invention:

Step 1: Preparing an aryl allyl ether by reacting a phenolic compound or a mixture of phenolic compounds with an allylation agent;

Step 2: Converting the aryl allyl ether of Step 1 above to an α-dihydroxy derivative;

Step 3: Halide substituting the α-dihydroxy derivative of Step 2 above to manufacture an α-halohydrin intermediate; and Step 4: Epoxidizing the α-halohydrin intermediate of Step 3 above by a ring-closure process using a base to convert the α-halohydrin intermediate of Step 3 to a phenol-based epoxy resin.

In one embodiment of the present invention, the above four-step process may be more specifically illustrated by the following general reaction sequence, Reaction Sequence (V), showing the manufacture of bisphenol A epoxy resin. More specifically, Reaction Sequence (V) shows the conversion of an aryl allyl ether to bisphenol A epoxy resin via the bis(α-chlorohydrin) intermediate made from an bis(α-dihydroxy) derivative.

Reaction Sequence (V)

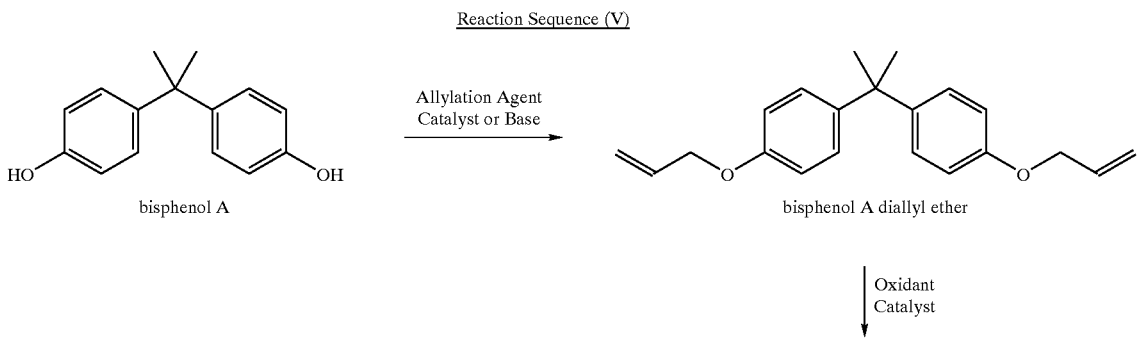

bisphenol A bisphenol A diallyl ether

Oxidant
Catalyst

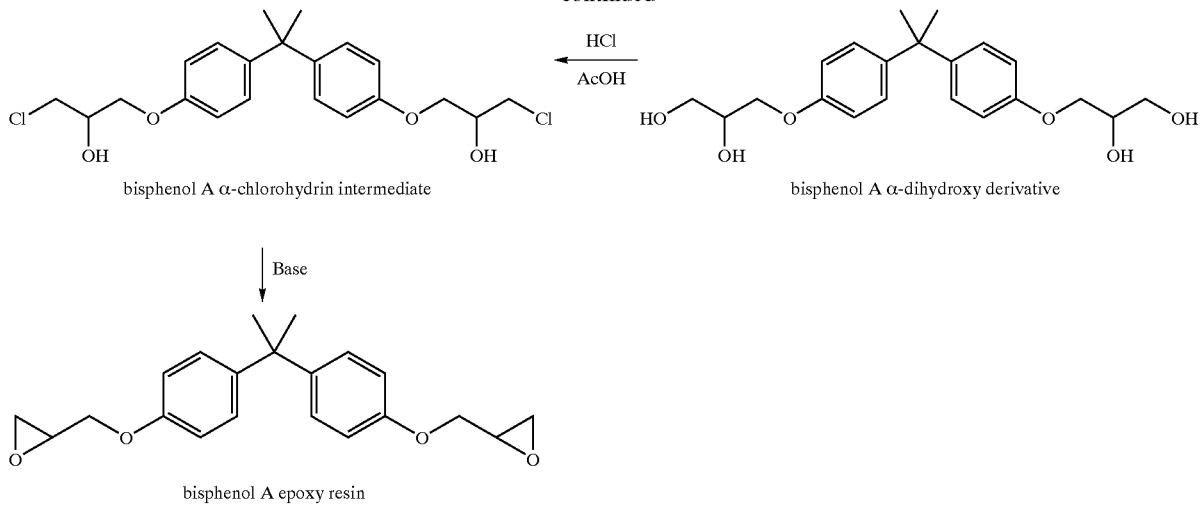

bisphenol A α-chlorohydrin intermediate bisphenol A α-dihydroxy derivative bisphenol A epoxy resin The epoxy resins prepared in the present invention may be used in various applications including for example, coatings, such as water-borne and solvent-borne coatings, can and coil coatings, powder coatings, industrial and marine protective coatings; adhesives; sealants; composites; and electrical applications, such as electrical laminates and electronic encapsulation.

EXAMPLE 1

A. Conversion of Bisphenol A to Bisphenol A Diallyl Ether

Bisphenol A diallyl ether was synthesized as described in U.S. Pat. No. 4,740,330. In a four-necked reactor, equipped with a condenser, stirrer, thermometer with temperature controller, and an addition funnel, were added 800 mL of bis-(2-methoxy ethyl) ether (diglyme), 400 mL of dimethyl sulfoxide (DMSO), 228 g (1 mole) bisphenol-A, and 284 g (4 moles) of 85% KOH at ambient temperature (~25° C.). The mixture was stirred and heated to 35–40° C., and the addition of 304 g (4 moles) of allyl chloride was begun. This reaction was exothermic and was controlled at less than 45° C. by controlling the allyl chloride addition rate. The allyl chloride was added over a 4-hour period, and the reaction was continued at 45° C. for an additional 12 hours to convert the bisphenol-A into diallyl ether. The reaction mixture was cooled to ambient temperature and filtered to remove salts formed in the reaction. The filtrate was mixed with 1000 mL of 50:50 (volume:volume) methyl ethyl ketone-toluene mixture and washed four times with 200 mL portions of water. The solvents were removed from the diallyl product by rotary evaporation first at 50–60° C. and 120 mmHg and then at 120–130° C. at 10 mmHg until gas chromatography (GC) showed all the diglyme and DMSO had disappeared. The yield was 235 g (76% yield) of a light yellow product, bis A diallyl ether, with greater than 95% purity as determined by GC.

B. Conversion of Bisphenol A Diallyl Ether to the Bis(α-dihydroxy) Derivative, Bis(2,3-α-dihydroxypropyl)ether of 4,4'-bisphenol A To a 100-mL, round-bottom flask, were added 1.005 g of bisphenol A diallyl ether from Part A above 10 mL of H$_2$O, 10 mL of tert-butanol and 1.78 mL of N-methyl morpholine N-oxide (50 wt % aqueous, 1.3 molar equivalents). The resulting reaction mixture was stirred at room temperature and then 0.02 g of K$_2$OsO$_4$·2H$_2$O (2 mol %) was added to the reaction mixture. The reaction mixture was stirred for 43 hours until all the starting material was reacted as determined by thin layer chromatography. Then 0.5 g of Na$_2$SO$_3$ and 0.5 g of diatomaceous earth were added to the reaction mixture. The reaction mixture was stirred an additional 1 hour and then filtered. The filtrate was extracted with 3 volumes of ethyl acetate. The resulting extracts were combined and dried over K$_2$CO$_3$ and Na$_2$SO$_4$, filtered, rotary evaporated, and dried under vacuum. The resulting white solid was analyzed by $^1$H NMR spectroscopy and contained 97 mol % of the bis(α-dihydroxy) derivative of bisphenol A diallyl ether and ca. About 3% of α-dihydroxy derivative of bisphenol A monoallyl ether. The white solid (1.052 g; 94% yield) was column chromatographed using a 1 inch by 9 inch silica gel column using ethyl acetate then acetone as the eluant system. Two fractions were isolated: a first fraction, 0.022 g (2.8%), and a second fraction, 0.761 g (97.2%). The fractions were analyzed by $^1$H NMR spectroscopy. The first fraction was the α-dihydroxy derivative of bisphenol A monoallyl ether derived from the monoallyl ether present as an impurity in the starting material. The second fraction was the desired bis(α-dihydroxy) derivative of bisphenol A, bis(2,3-α-dihydroxypropyl)ether of 4,4'-bisphenol A.

C. Conversion of Bisphenol A Diallyl Ether to the Bis(α-dihydroxy) Derivative, Bis(2,3-α-dihydroxypropyl)ether of 4,4'-bisphenol A To a 500-mL, round-bottom flask were added 10.30 g of bisphenol A diallyl ether from Part A above, 100 mL of H$_2$O, 100 mL of tert-butanol and 15.2 mL of N-methyl morpholine N-oxide (50 wt % aqueous, 1.2 molar equivalents). The resulting reaction mixture was stirred at room temperature and 0.231 g of K$_2$OsO$_4$·2H$_2$O (2 mol %) was added to the reaction mixture. The reaction mixture was allowed to stir for 18 hours. Then, 1.1 g of Na$_2$SO$_3$ and 1–2 g of diatomaceous earth were added to the reaction mixture. The reaction mixture was allowed to stir for an additional 1 hour and then filtered. The filtrate was saturated with NaCl, brought to a pH of 1 with concentrated HCl, and then extracted with 4 volumes of ethyl acetate. The resulting extracts were combined and dried over K$_2$CO$_3$ and Na$_2$SO$_4$, filtered, rotary evaporated, and dried under vacuum. The resulting solid was triturated with hexanes and filtered. The solids were further triturated with carbon tetrachloride, filtered and dried under vacuum. The resulting white solid (10.2 g; 84% yield), which was analyzed by $^1$H NMR spectroscopy contained 96 mol % dihydroxylated allyl ether.

D. Convesion of Bisphenol A Bis(α-dihydroxy) Derivative to the Bis(α-chlorohydrin) Intermediate, Bis(3-chloro-2-hydroxypropyl)ether of 4,4'-bisphenol A In this part of Example 1, a 100-ml, four-necked, glass reactor equipped with a cooling condenser connected to a gas scrubber containing 40% KOH, a thermometer, a magnetic stirrer, a fritted glass gas inlet tube, and a heating lamp with thermo-controller was employed. To the reactor were added 1 g (2.66 mmol) of crude bis(α-dihydroxy) derivative of bisphenol A from Part C above, 2.5 g (18.9 mmol) of 1-methoxy-2-propanol acetate as catalyst, and 15 g of 1-methoxy 2-propanol as solvent. The mixture was heated to 100–105° C. HCl gas was slowly bubbled into the mixture for about 5.5 hours after which time GC analysis showed greater than 95% of the bis(α-dihydroxy) derivative of bisphenol A was converted into the bis(α-chlorohydrin) intermediate of bisphenol A, the structure of which was confirmed by GC comparison with standard bisphenol A bis(α-chlorohydrin) obtained from the conventional coupling of bisphenol A and epichlorohydrin. The structure of the product bisphenol A bis(α-chlorohydrin), bis(3-chloro-2-hydroxypropyl)ether of 4,4'-bisphenol A, was further confirmed by HPLC/MS analysis, which is summarized in Table I below.

TABLE I

HPLC/MS analysis of bisphenol A bis(α-chlorohydrin) intermediate made from the bis(α-dihydroxy) derivative.

| Peak MW | Tentative Structure | Peak Area % |
|---|---|---|
| 376 | [structure] | 0.2 |
| 302 | [structure] | 0.3 |
| 418 | [structure] | 0.1 |
| 394 | [structure] | 6.2 |
| 320 | [structure] | 3.6 |
| 436 | [structure] | 1.4 |
| 408 | unknown | 0.1 |
| 504 | [structure] | 0.2 |
| 412a | [structure] | 79 |
| 412b | isomer of 412a | 0.3 |

TABLE I-continued

HPLC/MS analysis of bisphenol A bis(α-chlorohydrin) intermediate made from the bis(α-dihydroxy) derivative.

| Peak MW | Tentative Structure | Peak Area % |
|---|---|---|
| 450 | [structure: OH-CH$_2$-CH(OH)-CH$_2$-O-C$_6$H$_4$-C(CH$_3$)$_2$-C$_6$H$_4$-O-CH$_2$-CH(CH$_2$Cl)-CH$_2$-O-CH$_2$-CH(O)CH$_2$ epoxide] | 0.8 |
| 454 | [structure: Cl-CH$_2$-CH(OAc)-CH$_2$-O-C$_6$H$_4$-C(CH$_3$)$_2$-C$_6$H$_4$-O-CH$_2$-CH(OH)-CH$_2$-Cl] | 0.3 |
| 484 | unknown | 0.1 |
| 448 | unknown | 0.1 |
| 362 | unknown | 0.1 |

E. Conversion of Bisphenol A Bis(α-chlorohydrin) Intermediate to Bisphenol A Diglycidyl Ether Epoxy Resin In this part of Example 1, a 250-ml, four-necked, glass reactor equipped with a cooling condenser, a thermometer, a magnetic stirrer, an addition funnel for liquids, and a heating lamp with a thermo-controller was employed. Into the reactor was transferred crude bis(α-chlorohydrin) derivative of bisphenol A prepared via a chloride substitution process and described in Experiment C2 of Example 2 of U.S. Pat. No. 6,534,621, incorporated herein by reference. To the reactor was also added 100 g of 1-methoxy-2-hydroxypropane as solvent. At ambient temperature, 12 g of 50% aqueous NaOH solution (0.15 mole) was added slowly to the mixture over a period of 30 minutes, after which the mixture was allowed to react for about an additional 30 minutes in order to neutralize unreacted HCl dissolved in the mixture.

After removing the resulting precipitated salt by filtration, the resultant solution was transferred into another 250-mL, four-necked, glass reactor equipped with a cooling condenser, a thermometer, a magnetic stirrer, an addition funnel for liquids, and a heating lamp with a thermo-controller. The solution was heated to 50–52° C. Using the addition funnel, 12 g of 50% aqueous NaOH solution (0.15 mole) was added slowly to the heated solution over a period of 60 minutes at 50–52° C., after which time the resulting reaction mixture was allowed to react for about an additional 60 minutes at 50–52° C. GC analysis of the resultant product indicated that greater than 90% of the bis(α-chlorohydrin) derivative was converted into bisphenol A diglycidyl ether (BADGE) as identified by GC elution time comparison with an authentic commercial sample. The epoxy product was dissolved into 150 mL methyl ethyl ketone-toluene mixture (50:50, volume:volume) and was washed twice with 50 mL portions of water. The organic phase was separated and concentrated by rotary evaporation at 90–95° C. and less than 15 mmHg, yielding 13 g of epoxy resin having an epoxy content of 20.33% and an epoxy equivalent weight of 209. This reaction product was analyzed by high pressure liquid chromatography (HPLC)/mass spectrometry (MS) and the analysis of the major components is shown in Table II below.

TABLE II

HPLC/MS Analysis of Epoxidation Product of a Bisphenol A Bis(α-Chlorohydrin) Intermediate formed via a Chloride Substitution Process

| Peak ID (MW) | Tentative Structure | Peak Area % |
|---|---|---|
| 394 | [structure: Cl-CH$_2$-CH(OH)-CH$_2$-O-C$_6$H$_4$-C(CH$_3$)$_2$-C$_6$H$_4$-O-CH$_2$-CH(OH)-CH$_2$-OH] | 1.94% |
| 358 | [structure: epoxide CH$_2$-CH-CH$_2$-O-C$_6$H$_4$-C(CH$_3$)$_2$-C$_6$H$_4$-O-CH$_2$-CH(OH)-CH$_2$-OH] | 9.32% |

TABLE II-continued

HPLC/MS Analysis of Epoxidation
Product of a Bisphenol A Bis(α-Chlorohydrin) Intermediate
formed via a Chloride Substitution Process

| Peak ID (MW) | Tentative Structure | Peak Area % |
|---|---|---|
| 414a or 414b | [structure] | 2.06% |
| 400 | [structure] | 2.20% |
| | unknown | 2.67% |
| 376a | [structure] | 3.60% |
| 376b | [structure] | 3.70% |
| 340 | [structure] | 67.90% |
| 374 | unknown | 0.21% |
| 418 | [structure] | 0.51% |

EXAMPLE 2

A. Conversion of Phenyl Allyl Ether to 2,3-dihydroxypropyl Ether of Phenol

Phenyl allyl ether (1.0 mL) (from Aldrich) was suspended in 10 mL of $H_2O$ and 10 mL of tert-butanol in a 100-mL round-bottom flask, and 3.32 mL of N-methyl morpholine N-oxide (50 wt % aqueous; 1.1 molar equivalents) was added to the flask. The resulting reaction mixture was stirred at room temperature, and 0.025 g of $K_2OsO_4 \cdot 2H_2O$ (2 mol %) was added to the mixture. The reaction mixture was allowed to stir for 18 hours. Then 200 mg of $Na_2SO_3$ and 0.2 g of diatomaceous earth were added to the mixture. The reaction mixture was stirred an additional 1 hour and then filtered. The filtrate was extracted three times with 1 volume of ethyl acetate. The resulting extracts were combined, washed twice with 1 volume of 1 N HCl, washed with one volume of water, dried over $NaHCO_3$ and $Na_2SO_4$, filtered, rotary evaporated, and dried under vacuum. The resulting white solid (1.00 g; 82% yield), which was analyzed by $^1H$ NMR spectroscopy, was 98% pure 2,3-dihydroxypropyl ether of phenol.

B. Preparation of 3-chloro-2-hydroxypropyl Ether of Phenol from the α-dihydroxy Derivative of Phenol A 100-mL, four-necked, glass reactor equipped with a cooling condenser connected to a gas scrubber containing aqueous 40% KOH, a thermometer, a magnetic stirrer, a fritted glass gas dispersion tube, and a heating lamp with thermo-controller was employed. To the reactor were added 5 g (29.8 mmol) of the α-dihydroxy derivative of phenol (3-phenoxy-2,3-propanediol, purchased from Aldrich), 8 g (60.6 mmol) 1-methoxy-2-propanol acetate as a catalyst, and 20 cc of 1-methoxy 2-propanol as solvent. The mixture was heated to 100° C. HCl gas was slowly bubbled into the mixture for about 5 hours, after which time greater than 95% of the α-dihydroxy derivative of phenol was converted. The reaction product was washed from the reactor with two 100-mL portions of methylene chloride. The portions of methylene chloride extracts containing the crude reaction product were combined and washed once with 50 mL of water. The methylene chloride solution was concentrated under vacuum using rotary evaporation at 90° C. and less than 10 mmHg to yield about 4 g of colorless oil. Gas chromatography (GC) coupled with mass spectrometry (MS) analysis indicated that the major product formed in greater than 95% yield is the α-chlorohydrin intermediate (3-chloro-2-hydroxypropyl ether of phenol).

C. Conversion of α-chlorohydrin Intermediate of Phenol to Phenyl Glycidyl Ether

In this part of Example 2, a 100-mL, four-necked, glass reactor equipped with a cooling condenser, a thermometer, a magnetic stirrer, an addition funnel for liquids, and a heating lamp with a thermo-controller was employed. To the reactor was added 10 g of crude α-chlorohydrin intermediate of phenol prepared as described in Part C of Example 1 of U.S. Patent Application Serial No. 60/205,366, filed May 18, 2000, (Attorney Docket No. 60002), incorporated herein by reference. The crude α-chlorohydrin intermediate prepared via a chloride substitution process contains about 8.5 g of 3-chloro-2-hydroxypropyl ether of phenol and 1.5 g of 1-methoxy-2-acetoxypropane (the amounts are based on GC area % data). To the reactor was also added 20 g of 1-methoxy-2-hydroxypropane as solvent. The resultant reaction mixture was heated to 55° C. Using the addition funnel, 5.12 g of 50% aqueous NaOH solution (0.065 mole) was added slowly to the heated mixture over a period of 15 minutes after which the mixture was allowed to react for about an additional 20 minutes. GC analysis of the resultant product indicated that greater than 95% of the α-chlorohydrin intermediate was converted into phenyl glycidyl ether as identified by GC elution time comparison with an authentic sample of phenyl glycidyl ether. This reaction mixture of epoxy product was not further purified.

What is claimed is:

1. A process for making an epoxy compound or resin comprising:
   (a) converting an aryl allyl ether of a phenol or mixture of phenols to an α-dihydroxy derivative of a phenol or mixture of phenols (i) in the presence of an oxidant or (ii) in the presence of an oxidant and a catalyst;
   (b) reacting the α-dihydroxy derivative prepared in step (a) with a hydrogen halide and a carboxylic acid or a carboxylic acid ester to form a phenolic-based α-halohydrin intermediate, and
   (c) converting the phenolic-based α-halohydrin intermediate prepared instep (b) to an aryl glycidyl ether of a phenol or mixture of phenols as an epoxy compound or resin.

2. The process of claim 1 wherein the aryl allyl ether is represented by the structure of the following Formula I:

Formula I

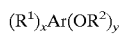

wherein Ar is an aromatic-containing moiety; $R^1$ is a group substituted for a hydrogen atom on the Ar moiety; $R^2$ is a propenyl-containing moiety; x is from 0 to 750; and y is from 1 to 150.

3. The process of claim 2 wherein the aryl allyl ether is one or more aryl allyl ethers represented by any one or more of the following Formulas II–V:

Formula II

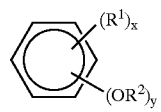

wherein $R^1$ is a group substituted for a hydrogen atom on the phenyl moiety; $R^2$ is a propenyl-containing moiety; x is from 0 to 5; and y is from 1 to 4;

Formula III

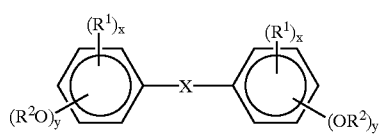

wherein $R^1$ is a group substituted for a hydrogen atom on the phenyl moiety; $R^2$ is a propenyl-containing moiety; X is a direct single bond, a heteroatom with or without substituents thereon to complete its necessary bonding valence, —C(O)—; —S(O$_2$)—; —C(O)NH—; —P(O)Ar—, wherein Ar is an aromatic group; an organic aliphatic moiety, with or without heteroatoms, and —CR$^3$=CH—, where $R^3$ is hydrogen or an alkyl group, a cycloaliphatic group or aromatic group; a cycloaliphatic group, with or without heteroatoms; or an aromatic group, with or without heteroatoms; or any combination thereof; partially or fully fluorinated; each x is from 0 to 4, and each x can be the same or different; and each y is from 1 to 4, and each y can be the same or different;

Formula IV

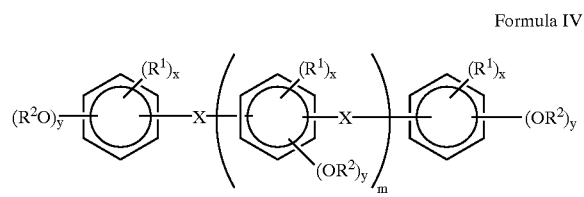

wherein $R^1$ is a group substituted for a hydrogen atom on the phenyl moiety; $R^2$ is a propenyl-containing moiety; X is a direct single bond, a heteroatom with or without substituents thereon to complete its necessary bonding valence, —C(O)—; —S(O$_2$)—; —C(O)NH—; —P(O)Ar—, wherein Ar is an aromatic group; an organic aliphatic moiety, with or without heteroatoms, and —CR$^3$=CH—, where $R^3$ is hydrogen or an alkyl group, a cycloaliphatic group or aromatic group; a cycloaliphatic group, with or without heteroatoms; or an aromatic group, with or without heteroatoms; or any combination thereof; partially or fully fluorinated; each x is from 0 to 4, and each x can be the same or different; each y is from 1 to 4, and each y can be the same or different; and m is from 0.001 to 10;

Formula V

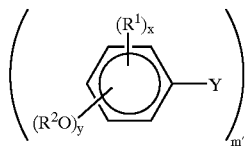

wherein $R^1$ is a group substituted for a hydrogen atom on the phenyl moiety; $R^2$ is a propenyl-containing moiety; Y is an organic aliphatic moiety, with or without heteroatoms such as O, N, S, Si, B or P, or any combination of two or more of the above heteroatoms, wherein the aliphatic moiety has from 1 to 20 carbon atoms; a cycloaliphatic moiety, with or without heteroatoms, having from 3 to 20 carbon atoms; an aromatic moiety, with or without heteroatoms; or any combination thereof, with nor more than about 20 carbon atoms; partially or fully fluorinated; an organosiloxane unit with the aryl groups attached to the Si atoms directly or through an organic aliphatic, cycloaliphatic, aromatic group, or any combination thereof, with no more than about 20 carbon atoms; each x is from 0 to 4, and each x can be the same or different; each y is from 1 to 4, and each y can be the same or different; and m' is generally 3 or 4.

4. The process of claim 3 wherein at least one $R^2$ is a monoalkylene oxide or a polyalkylene oxide terminated with a propenyl-containing moiety.

5. The process of claim 3 wherein $R^2$ is a propenyl-containing moiety selected from the group consisting of:

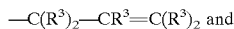

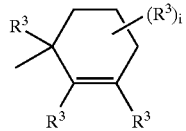

wherein each $R^3$ may be the same or different in each occurrence and is hydrogen or an alkyl group, a cycloaliphatic group or aromatic group; and i is from 0 to 6.

6. The process of claim 5 wherein $R^2$ in Formula II is —CH$_2$CH=CH$_2$, —CH$_2$C(CH$_3$)=CH$_2$ or

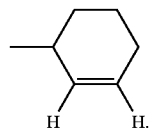

7. The process of claim 6 wherein $R^2$ in Formula II is —CH$_2$CH=CH$_2$.

8. The process of claim 3 wherein the aryl allyl ether is selected from the group consisting of 2-methyl phenyl allyl ether; 4-methyl phenyl allyl ether; 4-methoxyphenyl allyl ether; 2,6-dimethylphenyl allyl ether; 2,6-diisopropylphenyl allyl ether; 2,6-dibromophenyl allyl ether; 1,2-, 1,3-, 1,4-benzene diallyl ethers; 1,4-, 1,5- and 2,6-naphthalene diallyl ethers; 4,4'-(3,3',5,5'-tetramethyl)bisphenol A diallyl ether; 4,4'-(3,3',5,5'-tetramethyl-2,2',6,6'-tetrabromo)bisphenol A diallyl ether; 4,4'-(3,3',5,5'-tetramethyl)bisphenol F diallyl ether; 4,4'-(3,3',5,5'-tetramethyl)biphenol diallyl ether; 4,4'-biphenol diallyl ether; 4,4'-(3,3',5,5'-tetramethyl)biphenol diallyl ether; 4,4'-(3,3'5,5'-tetramethyl-2,2',6,6'-tetrabromobiphenol)diallyl ether; 4,4'-bisphenol F diallyl ether; 4,4'-bisphenol sulfone diallyl ether; 2,2'-bis (3,5-dibromo-4-hydroxy phenyl)isopropylidene diallyl ether; 4,4'-bisphenol A diallyl ether; 4,4'-bisphenol K diallyl ether; 9,9-bis(4-hydroxyphenyl)fluorene diallyl ether; 4,4'-dihydroxy-α-methylstilbene diallyl ether; 1,3-bis(4-hydroxyphenyl)adamantane diallyl ether; phenol-formaldehyde novolac allyl ether (functionality>2); o-cresol-formaldehyde novolac allyl ether (functionality>2); phenol-dicyclopentadienyl novolac allyl ether (functionality>2); naphthol-formaldehyde novolac allyl ether (functionality>2); trisphenylol methane triallyl ether; tris(3,5-dimethyl-4-hydroxyphenyl)methane triallyl ether; 1,1,2,2-tetraphenylol ethane tetraallyl ether; and a mixture thereof.

9. The process of claim 1 wherein the α-dihydroxy derivative of a phenol or mixture of phenols is represented by the structure of the following Formula XI:

Formula XI

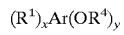

wherein Ar is an aromatic-containing moiety; $R^1$ is a group substituted for a hydrogen atom on the Ar moiety; $R^4$ is α-2,3-dihydroxy propyl-containing moiety; x is from 0 to 750; and y is from 1 to 150.

10. The process of claim 9 wherein the α-dihydroxy derivative of a phenol or mixture of phenols is represented by any one or more of the following Formulas XII–XV:

Formula XII

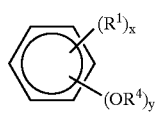

wherein $R^1$ is a group substituted for a hydrogen atom on the phenyl moiety; $R^4$ is an α-dihydroxy propyl-containing moiety; x is from 0 to 5; and y is from 1 to 4;

Formula XIII

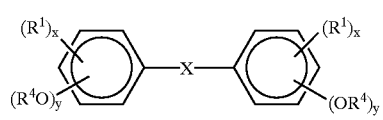

wherein $R^1$ is a group substituted for a hydrogen atom on the phenyl moiety; $R^4$ is an α-dihydroxy propyl-containing moiety; X is a direct single bond, a heteroatom with or without substituents thereon to complete its necessary bonding valence, —C(O)—; —S(O$_2$)—; —C(O)NH—; —P(O)Ar—, wherein Ar is an aromatic group; an organic aliphatic moiety, with or without heteroatoms, and —CR$^3$=CH—, where $R^3$ is hydrogen or an alkyl group, a cycloaliphatic group or aromatic group; a cycloaliphatic group, with or without heteroatoms; or an aromatic group, with or without heteroatoms; or any combination thereof; partially or fully fluorinated; each x is from 0 to 4, and each x can be the same or different; and each y is from 1 to 4, and each y can be the same or different;

Formula XIV

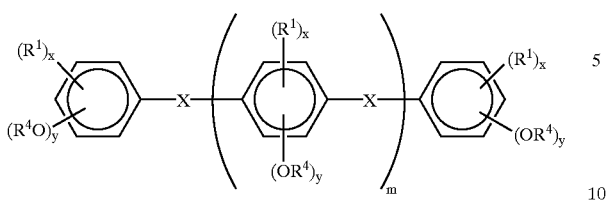

wherein R¹ is a group substituted for a hydrogen atom on the phenyl moiety; R⁴ is an α-dihydroxy propyl-containing moiety; X is a direct single bond, a heteroatom with or without substituents thereon to complete its necessary bonding valence, —C(O)—; —S(O₂)—; —C(O)NH—; —P(O)Ar—, wherein Ar is an aromatic group; an organic aliphatic moiety, with or without heteroatoms, and —CR³═CH—, where R³ is hydrogen or an alkyl group, a cycloaliphatic group or aromatic group; a cycloaliphatic group, with or without heteroatoms; or an aromatic group, with or without heteroatoms; or any combination thereof partially or fully fluorinated; x is from 0 to 4, and each x can be the same or different; each y is from 1 to 4, and each y can be the same or different; and m is from 0.001 to 10;

Formla XV

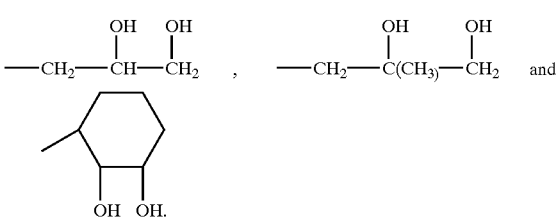

wherein R¹ is a group substituted for a hydrogen atom on the phenyl moiety; R⁴ is an α-dihydroxy propyl-containing moiety; Y is an organic aliphatic moiety, with or without heteroatoms such as O, N, S, Si, B or P, or any combination of two or more of the above heteroatoms, wherein the aliphatic moiety has from 1 to 20 carbon atoms; a cycloaliphatic moiety, with or without heteroatoms, having from 3 to 20 carbon atoms; an aromatic moiety, with or without heteroatoms; or any combination thereof, with no more than about 20 carbon atoms; partially or fully fluorinated; an organosiloxane unit with the aryl groups attached to the Si atoms directly or through an organic aliphatic, cycloaliphatic, aromatic group, or any combination thereof, with no more than about 20 carbon atoms; each x is from 0 to 4, and each x can be the same or different; each y is from 1 to 4, and each y can be the same or different; and m' is generally 3 or 4.

11. The process of claim 10 wherein at least one R⁴ is a monoalkylene oxide or a polyalkylene oxide terminated with a 2,3-dihydroxy propyl-containing moiety.

12. The process of claim 10 wherein R⁴ is a α-dihydroxy propyl-containing moiety selected from the group consisting of:

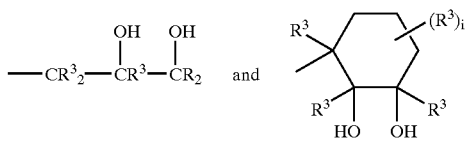

wherein R³ is the same or different in each occurrence and is hydrogen or an alkyl group, a cycloaliphatic group or aromatic group; and i is from 0 to 6.

13. The process of claim 12 wherein R⁴ is selected from the group consisting of:

14. The process of claim 13 wherein R⁴ is

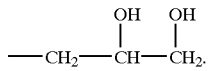

15. The process of claim 10 wherein α-dihydroxy derivative is selected from the group consisting of (2,3-α-dihydroxypropyl) ether of 2-methylphenol; (2,3-α-dihydroxypropyl)ether of 4-methylphenol; (2,3-1-dihydroxypropyl)ether of 4-methoxyphenol; (2,3-α-dihydroxypropyl)ether of 2,6-dimethylphenol; (2,3-α-dihydroxypropyl)ether of 2,6-diisopropylphenol; (2,3-1-dihydroxypropyl)ether of 2,6-dibromophenol; bis(2,3-α-dihydroxypropyl)ether of 1,2-, 1,3- and 1,4-dihydroxybenzene; bis(2,3-α-dihydroxypropyl)ether of 1,4-, 1,5- and 2,6-dihydroxynaphthalene; bis(2,3-α-dihydroxypropyl)ether of 4,4'-(3,3',5,5'-tetramethyl) bisphenol A; bis(2,3-α-dihydroxypropyl)ether of 4,4'-(3,3', 5,5'-tetramethyl-2,2',6,6'-tetrabromo)bisphenol A; bis(2,3-α-dihydroxypropyl)ether of 4,4'-(3,3',5,5'-tetramethyl) bisphenol F; bis(2,3-α-dihydroxypropyl)ether of 4,4'-(3,3'5, 5'-tetramethyl)biphenol; bis(2,3-α-dihydroxypropyl)ether of 4,4'-biphenol; bis(2,3-α-dihydroxypropyl)ether of 4,4'-(3, 3'5,5'-tetramethyl-2,2',6,6'-tetrabromo)biphenol; bis(2,3-α-dihydroxypropyl)ether of 4,4'-bisphenol F; bis(2,3-α-dihydroxypropyl)ether of 4,4'-bisphenol sulfone; bis(2,3-α-dihydroxypropyl)ether of 2,2'-bis(3,5-dibromo-4-hydroxyphenyl)isopropylidene; bis(2,3-α-dihydroxypropyl) ether of 4,4'-bisphenol A; bis(2,3-α-dihydroxypropyl)ether of 4,4'-bisphenol K; bis(2,3-α-dihydroxypropyl)ether of 9,9-bis(4-hydroxyphenyl)fluorene; bis(2,3-α-dihydroxypropyl) ether of 4,4'-dihydroxy-α-methylstilbene; bis(2,3-α-dihydroxypropyl)ether of 1,3-bis(4-hydroxyphenyl) adamantane; (2,3-α-dihydroxypropyl)ether of phenol-formaldehyde novolac (functionality>2); (2,3-α-dihydroxypropyl)ether of o-cresol-formaldehyde novolac (functionality>2); (2,3-α-dihydroxypropyl)ether of phenol-dicyclopentadienyl novolac (functionality>2); (2,3-α-dihydroxypropyl)ether of naphthol-formaldehyde novolac (functionality>2); tris(2,3-α-dihydroxypropyl)ether of trisphenylol methane; tris(2,3-α-dihydroxypropyl)ether of tris(3,5-dimethyl-4-hydroxyphenyl)methane; tetra(2,3-α-dihydroxypropyl)ether of 1,1,2,2-tetraphenylol ethane; and mixtures thereof.

16. The process of claim 1 wherein the aryl glycidyl ether epoxy resin compound of a phenol or mixture of phenols is represented by the structure of the following Formula XVI:

Formula XVI

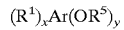

wherein Ar is an aromatic-containing moiety; R¹ is a group substituted for a hydrogen atom on the Ar moiety; $R^5$ is glycidyl-containing moiety; x is from 0 to 750; and y is from 1 to 150.

17. The process of claim 16 wherein the aryl glycidyl ether epoxy resin compound is one or more compounds represented by any one or more of the following Formulas XVII–XX;

Formula XVII

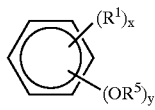

wherein $R^1$ is a group substituted for a hydrogen atom on the phenyl moiety; $R^5$ is glycidyl-containing moiety; x is from 0 to 5; and y is from 1 to 4;

Formula XVIII

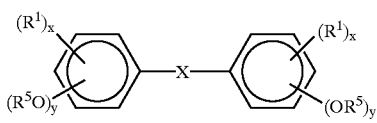

wherein $R^1$ is a group substituted for a hydrogen atom on the phenyl moiety; $R^5$ is glycidyl-containing moiety; X is a direct single bond, a heteroatom with or without substituents thereon to complete its necessary bonding valence, —C(O)—; —S(O$_2$)—; —C(O)NH—; —P(O)Ar—, wherein Ar is an aromatic group; an organic aliphatic moiety, with or without heteroatoms, and —CR$^3$=CH—, where $R^3$ is hydrogen or an alkyl group, a cycloaliphatic group or aromatic group; a cycloaliphatic group, with or without heteroatoms; or an aromatic group, with or without heteroatoms; or any combination thereof; partially or fully fluorinated; each x is from 0 to 4, and each x can be the same or different; and each y is from 1 to 4, and each y can be the same or different;

Formula XIX

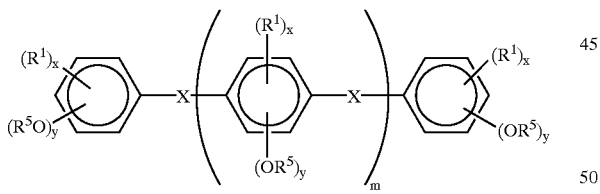

wherein $R^1$ is a group substituted for a hydro en atom on the phenyl moiety; $R^5$ is glycidyl-containing moiety; X is a direct single bond, a heteroatom with or without substituents thereon to complete its necessary bonding valence, —C(O)—; —S(O$_2$)—; —C(O)NH—; —P(O)Ar—, wherein Ar is an aromatic group; an organic aliphatic moiety, with or without heteroatoms, and —CR$^3$=CH—, where $R^3$ is hydrogen or an alkyl group, a cycloaliphatic group or aromatic group; a cycloaliphatic group, with or without heteroatoms; or an aromatic group, with or without heteroatoms; or any combination thereof; partially or fully fluorinated; x is from 0 to 4, and each x can be the same or different; each y is from 1 to 4, and each y can be the same or different; and m is from 0.001 to 10;

Formla XX

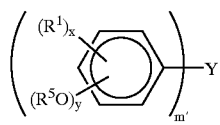

wherein $R^1$ is a group substituted for a hydrogen atom on the phenyl moiety; $R^5$ is glycidyl-containing moiety; Y is an organic aliphatic moiety, with or without heteroatoms such as O, N, S, Si, B or P, or any combination of two or more of the above heteroatoms, wherein the aliphatic moiety has from 1 to 20 carbon atoms; a cycloaliphatic moiety, with or without heteroatoms, having from 3 to 20 carbon atoms; an aromatic moiety, with or without heteroatoms; or any combination thereof, with no more than about 20 carbon atoms; partially or fully fluorinated; an organosiloxane unit with the aryl groups attached to the Si atoms directly or through an organic aliphatic, cycloaliphatic, aromatic group, or any combination thereof, with no more than about 20 carbon atoms; each x is from 0 to 4, and each x can be the same or different; each y is from 1 to 4, and each y can be the same or different; and m' is generally 3 or 4.

18. The process of claim 17 wherein at least one $R^5$ is a monoalkylene oxide or a polyalkylene oxide terminated with a propenyl-containing moiety.

19. The process of claim 17 wherein $R^5$ is a glycidyl-containing moiety selected from the group consisting of:

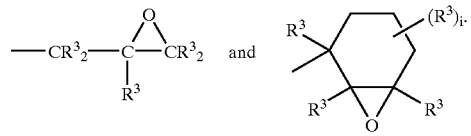

wherein each $R^3$ may be the same or different in each occurrence and is hydrogen or an alkyl group, a cycloaliphatic group or aromatic group; and i is from 0 to 6.

20. The process of claim 19 wherein $R^5$ is

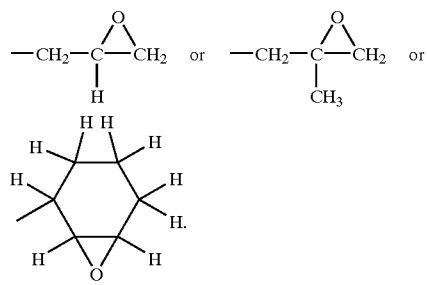

21. The process of claim 20 wherein $R^5$ is

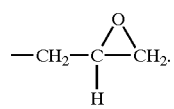

22. The process of claim 17 wherein the aryl glycidyl ether epoxy resin compound of a phenol or mixture of phenols is selected from the group consisting of 2-methylphenol glycidyl ether; 4-methylphenol glycidyl ether; 4-methoxyphenol glycidyl ether; 2,6-dimethylphenol glycidyl ether; 2,6-diisopropylphenol glycidyl ether; 2,6-dibromophenol glycidyl ether; 1,2-, 1,3- and 1,4-dihydroxybenzene diglycidyl ethers; 1,4-, 1,5- and 2,6-dihydroxynaphthalene diglycidyl ethers; 4,4'-(3,3',5,5'-tetramethyl)bisphenol A diglycidyl ether; 4,4'-(3,3',5,5'-tetramethyl-2,2',6,6'-tetrabromo)bisphenol A diglycidyl ether; 4,4'-(3,3',5,5'-tetramethyl)bisphenol F diglycidyl ether; 4,4'-(3,3'5,5'-tetramethyl)biphenyl diglycidyl ether; 4,4'-biphenol diglycidyl ether; 4,4'-(3,3'5,5'-tetramethyl-2,2',6,6'-tetrabromo)biphenyl diglycidyl ether; 4,4'-bisphenol F diglycidyl ether; 4,4'-bisphenol sulfone diglycidyl ether; 4,4'-(3,3',5,5'-tetrabromo)bisphenol A diglycidyl ether; 4,4'-bisphenol A diglycidyl ether; 4,4'-bisphenol K diglycidyl ether; 9,9-bis(4-hydroxyphenyl)fluorene diglycidyl ether; 4,4'-dihydroxy-α-methylstilbene diglycidyl ether; 1,3-bis(4-hydroxyphenyl)adamantane diglycidyl ether; phenol-formaldehyde novolac glycidyl ether (functionality>2); o-cresol-formaldehyde novolac glycidyl ether (functionality>2); phenol-dicyclopentadienyl novolac glycidyl ether (functionality>2); naphthol-formaldehyde novolac glycidyl ether (functionality>2); trisphenylol methane triglycidyl ether; tris(3,5-dimethyl-4-hydroxyphenyl) methane triglycidyl ether; 1,1,2,2-tetraphenylol ethane tetraglycidyl ether; or mixtures thereof.

23. A process of claim 1, for making an α-dihydroxy derivative of a phenol or mixture of phenols comprising converting an aryl allyl ether of a phenol or mixture of phenols to an α-dihydroxy derivative of a phenol or mixture of phenols in the presence of an oxidant.

24. The process of claim 23 wherein the oxidant is an aromatic or aliphatic organic peracid, an organic peroxyimidic acid, an organic N-oxide, a selenic peracid, a persulfates or a dioxirane.

25. The process of claim 23 wherein the oxidant is an oxidizing metal salt.

26. The process of claim 25 wherein the oxidizing metal salt is selected from the group comprising oxides of osmium, $K_3Fe(CN)_6$, and $KIO_4$.

27. The process of claim 23 wherein the ratio of the oxidant used for dihydroxylation of the aryl allyl ether is in the range of from about 0.6 mole to about 20 moles of oxidant to 1 equivalent of aryl allyl ether.

28. A process of claim 1, for making an α-dihydroxy derivative of a phenol or mixture of phenols comprising converting an aryl allyl ether of a phenol or mixture of phenols to an α-dihydroxy derivative of a phenol or mixture of phenols in the presence of an oxidant and a catalyst.

29. The process of claim 28 wherein the oxidant is air, oxygen, oxygen-gas(es) mixture(s), hydrogen peroxide, a tertiary organic amine N-oxide, an organic hydroperoxide, a periodate salt, a hypochlorite salt, a persulfate salt, or an iron (III) salt.

30. The process of claim 29 wherein the oxygen in the dihydroxylation reaction is present as pure oxygen or the oxygen is present as a mixture of gases.

31. The process of claim 30 wherein oxygen is present in the dihydroxylation reaction as a mixture of oxygen and nitrogen with oxygen being from about 1% to about 100% on a volume basis.

32. The process of claim 29 wherein the tertiary organic amine N-oxide has the general structure

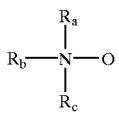

wherein $R_a$, $R_b$, and $R_c$ are each independently selected from the group consisting of an alkyl group, a cycloaliphatic group, an aromatic group, and a combination thereof have from 1 to 12 carbon atoms; and wherein $R_a$, $R_b$, and $R_c$ are the same or different.

33. The process of claim 32 wherein the organic amine N-oxides is selected from the group consisting of trimethylamine N-oxide, triethylamine N-oxide, N-methyl morpholine N-oxide, pyridine N-oxide, and mixtures thereof.

34. The process of claim 29 wherein the organic hydroperoxide has the general structure

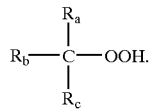

wherein $R_a$, $R_b$, and $R_c$ are each independently selected from the group consisting of an alkyl group, a cycloaliphatic group, an aromatic group, and a combination thereof have from 1 to 12 carbon atoms; and $R_a$, $R_b$, and $R_c$ are the same or different.

35. The process of claim 34 wherein the organic hydroperoxide is selected from the group consisting of tert-butyl hydroperoxide; tert-amyl hydroperoxide; cumene hydroperoxide; ethyl benzene hydroperoxide; cyclohexane hydroperoxide; methyl cyclohexane hydroperoxide; pinane hydroperoxide; tetrahydronaphthalene hydroperoxide; isobutyl benzene hydroperoxide; isopropyl hydroperoxide; and ethyl naphthalene hydroperoxide; and mixtures thereof.

36. The process of claim 28 wherein the ratio of the oxidant used for catalytic dihydroxylation of the aryl allyl ether is in the range of from about 0.6 mole to 20 moles of oxidant to 1 equivalent of aryl allyl ether.

37. The process of claim 1, wherein the catalyst is a transition metal-containing catalyst or a Group VIB element-containing catalyst.

38. The process of claim 37 wherein the transition metal is selected from the group consisting of Group IVA, Group VA, Group VIA, Group VILA, and Group VIII transition metals.

39. The process of claim 38 wherein the transition metal or Group VIB element comprises a metal or element selected from the group consisting of Os, Mn, Re, Ru, W, Cr, Mo, V, Ti, Se, Bi, Ni, Cu, Sb, Fe, Tl, Pb, Rh, and Te.

40. The process of claim 39 wherein the transition metal is selected from the group consisting of Os, Mn, and Ru.

41. The process of claim 37 wherein the transition metal-containing catalyst or Group VIB element-containing catalyst a α-dihydroxylation catalyst is soluble and is a homogeneous catalyst.

42. The process of claim 37 wherein the transition metal-containing catalyst or and Group VIB element-containing catalyst useful as a α-dihydroxylation catalyst is bound covalently or ionically to a solid support and is a heterogenous catalyst.

43. The process of claim 41 wherein the molar ratio of transition metal-containing catalyst or Group VIB element-containing catalyst to aryl allyl ether present in the reaction mixture is from about $1\times10^{-6}$ to about 1 mole of catalyst per 1 mole of aryl allyl ether.

44. The process of claim 42 wherein the total weight of the metal or element in the catalyst to the total weight of the solid support material is in the range of from about $1 \times 10^{-6}$ parts to about 1 part of metal or element per 1 part of solid support.

45. The process of claim 44 wherein the weight ratio of heterogeneous catalyst to substrate aryl allyl ether is in the range of from about 100 parts to about $10^{-3}$ parts of heterogeneous catalyst to 1 part of aryl allyl ether.

46. The process of claim 1, wherein an additive, a co-catalyst or a co-oxidant is used together with the oxidant and catalyst.

47. The process of claim 46 wherein the additive is a pH regulator to control pH between about 7.5 to about 13.

48. The process of claim 47 wherein the additive is a tertiary amine or a diamine.

49. The process of claim 46 wherein the co-catalyst is a hydrolysis aid.

50. The process of claim 49 wherein the co-catalyst hydrolysis aid is methanesulfonamide or a salt of an alkyl sulfonamide or an alkyl carboxylate.

51. The process of claim 46 wherein the co-oxidant is a salt or a complex of Cu I, Cu II, V, Nb, Ta, Ti, Zr, Hf, W, or Mo.

52. The process of claim 46 wherein the co-oxidant is a naturally occurring flavone or a synthetic analog thereof.

53. The process of claim 46 wherein the additive, co-catalyst, or co-oxidant is used in the range of from about $1 \times 10^{-3}$ mole to about 0.20 mole of additive, co-catalyst, or co-oxidant per 1 equivalent of allyl ether group.

54. A process of claim 1, wherein in step (a) of converting an aryl allyl ether of a phenol or mixture of phenols to an α-dihydroxy derivative of a phenol or mixture of phenols, the temperature of the dihydroxylation reaction is from about −20° C. to about 150° C.

55. A process of claim 1, wherein in step (a) of converting an aryl allyl ether of a phenol or mixture of phenols to an α-dihydroxy derivative of a phenol or mixture of phenols, the pressure is sub-atmospheric, atmospheric, or super-atmospheric.

56. A process of claim 1, wherein in step (a) of converting an aryl allyl ether of a phenol or mixture of phenols to an α-dihydroxy derivative of a phenol or mixture of phenols, the dihydroxylation reaction is done optionally in the presence of a solvent.

57. The process of claim 56 wherein the solvent is selected from the group consisting of an aliphatic, cycloaliphatic and aromatic hydrocarbon, ester, ether, alcohol and nitrile solvent; partially and fully halogenated aliphatic, cycloaliphatic and aromatic hydrocarbon, ester, ether, alcohol and nitrile solvent; ketone; water; and combinations thereof.

58. The process of claim 56 wherein the solvent is employed in an amount of from about 0 parts by weight to about 100 parts by weight of solvent per one part of substrate reactant aryl allyl ether.

59. The process of claim 1 in which the amount of hydrogen halide used is from about 0.5 to about 20 equivalents of hydrogen halide relative to the equivalents of α-dihydroxy moieties being reacted.

60. The process of claim 1 in which the hydrogen halide is hydrogen chloride.

61. The process of claim 1 wherein the carboxylic acid used in (b) is from about 0.05 mole % to about 50 mole % of carboxylic acid relative to the moles of α-dihydroxy derivative being reacted.

62. The process of claim 1 wherein the carboxylic acid used in (b) is monocarboxylic acid or dicarboxylic acid having from 1 to 20 carbon atoms; or a multifunctional carboxylic acid wherein the carboxylic acid groups are attached to an inorganic, an organic, or a hybrid inorganic-organic support.

63. The process of claim 62 wherein the carboxylic acid is selected from the group consisting of acetic acid, propionic acid, propenoic acid, 2-methylpropenoic acid, butanoic acid, 1,4-butanedioic acid, hexanoic acid, 1,6-hexanedioic acid, cyclohexanoic acid, 1,2-cyclohexandioic acid, benzoic acid, and mixtures thereof.

64. The process of claim 63 wherein the carboxylic acid is acetic acid.

65. The process of claim 1 wherein a carboxylic acid ester is used in (b) to convert the α-dihydroxy derivative to the α-halohydrin intermediate.

66. The process of claim 65 wherein the carboxylic acid ester used is from about 0.05 mole % to about 50 mole % of carboxylic acid ester relative to the moles of α-dihydroxy derivative being reacted.

67. The process of claim 1 wherein the carboxylic acid ester is used as a solvent in (b) to convert the α-dihydroxy derivative to the α-halohydrin intermediate.

68. The process of claim 67 wherein the amount of carboxylic acid ester used as solvent is from about 0.25 to about 100 parts (on a weight basis) of carboxylic acid ester to 1 part α-dihydroxy derivative.

69. The process of claim 1 wherein the carboxylic acid ester is the ester of a monocarboxylic acid or dicarboxylic acid having 1 to 20 carbon atoms.

70. The process of claim 69 wherein the monocarboxylic acid or dicarboxylic acid contains one or more heteroatoms selected from the group consisting of O, N, S, Si, B, P, Cl and F.

71. The process of claim 69 wherein the monocarboxylic acid or dicarboxylic acid of the carboxylic acid ester is selected from the group consisting of acetic acid, propionic acid, propenoic acid, 2-methylpropenoic acid, butanoic acid, 1,4-butanedioic acid, hexanoic acid, 1,6-hexanedioic acid, cyclohexanoic acid, 1,2-cyclohexandioic acid, benzoic acid, and mixtures thereof.

72. The process of claim 1 wherein the carboxylic acid ester is the ester of an aliphatic mono alcohol, diol, or triol having 1 to 12 carbon atoms.

73. The process of claim 72 wherein the hydroxyl group (s) of the aliphatic mono alcohol, diol, or triol is a primary or secondary hydroxyl group.

74. The process of claim 72 wherein the aliphatic mono alcohol, diol, or triol contains one or more heteroatoms selected from the group consisting of O, N, S, Si, B, P, Cl and F.

75. The process of claim 73 wherein the aliphatic mono alcohol, diol, or triol is selected from the group consisting of methanol, ethanol, propanol, isopropanol, 1-butanol, 2-butanol, isobutanol, cyclohexanol, benzyl alcohol, 1-methoxy-2-propanol, 1-ethoxy-2-propanol, ethylene glycol, diethylene glycol, propylene glycol, diproplene glycol, glycerine, trimethylolpropane and mixtures thereof.

76. The process of claim 1 wherein the carboxylic acid ester is selected from the group consisting of ethyl acetate, propyl acetate, isopropyl acetate, 1-methoxy-2-propanol acetate, butyl acetate, ethylene glycol diacetate, propylene glycol diacetate, trimethylolpropane triacetate and mixtures thereof.

77. The process of claim 1 including at least one or more optional solvents.

78. The process of claim 77 wherein the at least one or more solvents are selected from the group consisting of aliphatic and cyclic hydrocarbons; aromatic hydrocarbons; chlorinated solvents; aprotic solvents; protic solvents; partially and fully fluorinated derivatives thereof; and any combination thereof.

79. The process of claim 78 wherein the protic solvents are secondary or tertiary alcoholic solvents.

80. The process of claim 78 wherein the at least one or more solvents are selected from the group consisting of pentane, hexane, octane, iso-octane, cyclohexane, cyclooctane, benzene, toluene, methylene dichloride, tetrachloroethane, chlorobenzene, acetone, methyl iso-butyl ketone, acetonitrile, dimethoxyethane, 2,2'-dimethoxy diethyl ether, dioxane, dimethyl sulfoxide, 1-methoxy-2-acetoxypropane, isopropyl alcohol, 2-butanol, tert-butanol, tert-amyl alcohol, cyclohexanol, and 1-methoxy-2-hydroxypropane; partially and fully fluorinated derivatives thereof; and any combination thereof.

81. The process of claim 77 wherein the at least one or more solvents may be used with or without the presence of water.

82. The process of claim 77 wherein the amount of the at least one or more solvents is from zero to about 50 parts (on a weight basis) of a single solvent or a mixture of two or more solvents to 1 part α-dihydroxy derivative.

83. The process of claim 67 including an amount of carboxylic acid ester used as solvent, and an amount of at least one or more optionally used second solvents such that the carboxylic acid ester is present in an amount that is greater than 25 mole % relative to the amount of α-dihydroxy derivative.

84. The process of claim 1 wherein the phenolic-based α-halohydrin intermediate is represented by the structure of the following Formula XXI:

Formula XXI

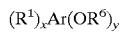

wherein Ar is an aromatic-containing moiety; $R^1$ is a group substituted for a hydrogen atom on the Ar moiety; $R^6$ is α-chlorohydrin propyl-containing moiety; x is from 0 to 750; and y is from 1 to 150.

85. The process of claim 84 wherein the α-halohydrin intermediate is one or more α-halohydrin intermediates represented by any one or more of the following Formulas XXII–XXV:

Formula XXII

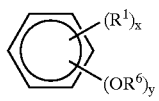

wherein $R^1$ is a group substituted for a hydrogen atom on the phenyl moiety; $R^6$ an α-chlorohydrin propyl-containing moiety; x is from 0 to 5; and y is from 1 to 4;

Formula XXIII

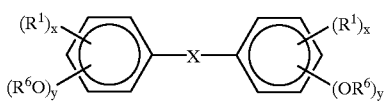

wherein $R^1$ is a group substituted for a hydrogen atom on the phenyl moiety; $R^6$ is an α-chlorohydrin propyl-containing moiety; X is a direct single bond, a heteroatom with or without substituents thereon to complete its necessary bonding valence, —C(O)—; —S(O$_2$)—; —C(O)NH—; —P(O)Ar—, wherein Ar is an aromatic group; an organic aliphatic moiety, with or without heteroatoms, and —CR$^3$═CH—, where $R^3$ is hydrogen or an alkyl group, a cycloaliphatic group or aromatic group; a cycloaliphatic group, with or without heteroatoms; or an aromatic group, with or without heteroatoms; or any combination thereof; partially or fully fluorinated; each x is from 0 to 4, and each x can be the same or different; and each y is from 1 to 4, and each y can be the same or different;

Formula XXIV

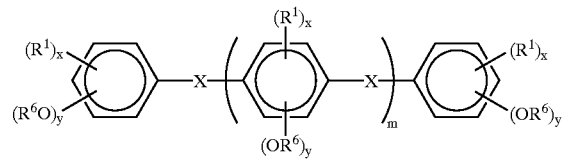

wherein $R^1$ is a group substituted for a hydrogen atom on the phenyl moiety; $R^6$ is an α-chlorohydrin propyl-containing moiety; X is a direct single bond, a heteroatom with or without substituents thereon to complete its necessary bonding valence, —C(O)—; —S(O$_2$)—; —C(O)NH—; —P(O)Ar—, wherein Ar is an aromatic group; an organic aliphatic moiety, with or without heteroatoms, and —CR$^3$═CH—, where $R^3$ is hydrogen or an alkyl group, a cycloaliphatic group or aromatic group; a cycloaliphatic group, with or without heteroatoms; or an aromatic group, with or without heteroatoms; or any combination thereof; partially or fully fluorinated; x is from 0 to 4, and each x can be the same or different; each y is from 1 to 4, and each y can be the same or different; and m is from 0.001 to 10;

Formula XXV

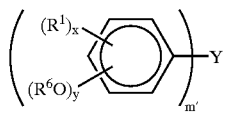

wherein $R^1$ is a group substituted for a hydrogen atom on the phenyl moiety; $R^6$ is an α-chlorohydrin propyl-containing moiety; Y is an organic aliphatic moiety, with or without heteroatoms such as O, N, S, Si, B or P, or any combination of two or more of the above heteroatoms, wherein the aliphatic moiety has from 1 to 20 carbon atoms; a cycloaliphatic moiety, with or without heteroatoms, having from 3 to 20 carbon atoms; an aromatic moiety, with or without heteroatoms; or any combination thereof, with no more than about 20 carbon atoms; partially or fully fluorinated; an organosiloxane unit with the aryl groups attached to the Si atoms directly or through an organic aliphatic, cycloaliphatic, aromatic group, or any combination thereof, with no more than about 20 carbon atoms; each x is from 0 to 4, and each x can be the same or different; each y is from 1 to 4, and each y can be the same or different; and m' is generally 3 or 4.

86. The process of claim 85 wherein at least one $R^6$ is a monoalkylene oxide or a polyalkylene oxide terminated with a propenyl-containing moiety.

87. The process of claim 85 wherein $R^6$ is a αhalohydrin propyl-containing moiety selected from the group consisting of:

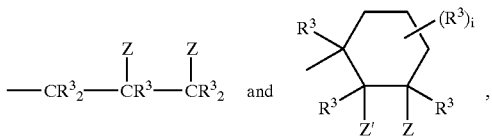

wherein Z is a halogen atom; Z' is a hydroxyl group; $R^3$ is the same or different in each occurrence and is hydrogen or an alkyl group, a cycloaliphatic group or aromatic group; and i is from 0 to 6.

88. The process of claim 87 wherein the positions of the Z group and the Z' group may be interchanged.

89. The process of claim 86 wherein $R^6$ is selected from the group consisting of:

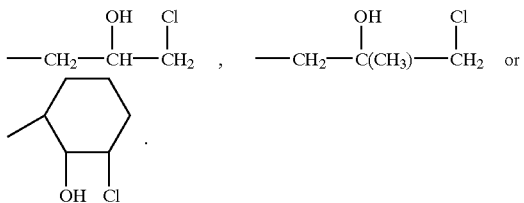

90. The process of claim 89 wherein $R^6$ is

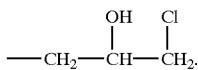

91. The process of claim 85 wherein α-halohydrin intermediate is a chlorohydrin intermediate selected from the group consisting of (3-chloro-2-hydroxy-1-propyl) ether of 2-methylphenol; (3-chloro-2-hydroxy-1-propyl) ether of 4-methylphenol; (3-chloro-2-hydroxy-1-propyl) ether of 4-)methoxyphenol; (3-chloro-2-hydroxy-1-propyl) ether of 2,6-dimethylphenol; (3-chloro-2-hydroxy-1-propyl) ether of 2,6-diisopropylphenol; (3-chloro-2-hydroxy-1-propyl) ether of 2,6-dibromophenol; bis(3-chloro-2-hydroxy-1-propyl) ether of 1,2-, 1,3- and 1,4-dihydroxybenzene; bis(3-chloro-2-hydroxy-1-propyl) ether of 1,4-, 1,5-and 2,6-dihydroxynaphthalene; bis(3-chloro-2-hydroxy-1-propyl) ether of 4,4'-(3,3',5,5'-tetramethyl)bisphenol A; bis(3-chloro-2-hydroxy-1-propyl) ether of 4,4'-(3,3',5,5'-tetramethyl-2,2',6,6'-tetrabromo)bisphenol A; bis(3-chloro-2-hydroxy-1-propyl)ether of 4,4'-(3,3',5,5'-tetramethyl)bisphenol F; bis(3-chloro-2-hydroxy-1-propyl) ether of 4,4'-(3,3'5,5'-tetramethyl)bisphenol; bis(3-chloro-2-hydroxy-1-propyl) ether of 4,4'-bisphenol; bis(3-chloro-2-hydroxy-1-propyl) ether of 4,4'-(3,3'5,5'-tetramethyl-2,2',6,6'-tetrabromo)bisphenol; bis(3-chloro-2-hydroxy-1-propyl) ether of 4,4'-bisphenol F; bis(3-chloro-2-hydroxy-1-propyl) ether of 4,4'-bisphenol sulfone; bis(3-chloro-2-hydroxy-1-propyl) ether of 2,2'-bis(3,5-dibromo-4-hydroxyphenyl)isopropylidene; bis(3-chloro-2-hydroxy-1-propyl) ether of 4,4'-bisphenol A; bis(3-chloro-2-hydroxy-1-propyl)ether of 4,4'-bisphenol K; bis(3-chloro-2-hydroxy-1-propyl) ether of 9,9-bis(4-hydroxyphenyl)fluorene; bis(3-chloro-2-hydroxy-1-propyl) ether of 4,4'-dihydroxy-α-methylstilbene; bis(3-chloro-2-hydroxy-1-propyl) ether of 1,3-bis(4-hydroxyphenyl)adamantane; (3-chloro-2-hydroxy-1-propyl) ether of phenol-formaldehyde novolac (functionality>2); (3-chloro-2-hydroxy-1-propyl) ether of o-cresol-formaldehyde novolac (functionality>2); (3-chloro-2-hydroxy-1-propyl) ether of phenol-dicyclopentadienyl novolac (functionality>2); (3-chloro-2-hydroxy-1-propyl) ether of naphthol-formaldehyde novolac (functionality>2); tri(3-chloro-2-hydroxy-1-propyl) ether of trisphenylol methane; tri(3-chloro-2-hydroxy-1-propyl) ether of tris(3,5-dimethyl-4-hydroxyphenyl)methane; tetra-(3-chloro-2-hydroxy-1-propyl) ether of 1,1,2,2-tetraphenylol ethane; and mixtures thereof.

92. The process of claim 91 wherein in at least one of the 3-chloro-2-hydroxy-1-propyl moieties, the chlorine atom and the hydroxy group of the α-chlorohydrin intermediate are interchanged to form a 2-chloro-3-hydroxy-1-propyl moiety.

* * * * *